United States Patent [19]

Maris et al.

[11] Patent Number: 5,748,317
[45] Date of Patent: May 5, 1998

[54] APPARATUS AND METHOD FOR CHARACTERIZING THIN FILM AND INTERFACES USING AN OPTICAL HEAT GENERATOR AND DETECTOR

[75] Inventors: Humphrey J Maris, Barrington, R.I.; Robert J Stoner, Duxbury, Mass.

[73] Assignee: Brown University Research Foundation, Providence, R.I.

[21] Appl. No.: 786,706

[22] Filed: Jan. 21, 1997

[51] Int. Cl.$^6$ ...................................................... G01B 9/02
[52] U.S. Cl. ...................... 356/357; 356/349; 356/432 T; 356/381
[58] Field of Search ............................. 356/432, 432 T, 356/381, 357, 349

[56] References Cited

U.S. PATENT DOCUMENTS

| | | | |
|---|---|---|---|
| 4,484,820 | 11/1984 | Rosencwaig | 374/6 |
| 4,522,510 | 6/1985 | Rosencwaig et al. | 374/7 |
| 4,579,463 | 4/1986 | Rosencwaig et al. | 374/57 |
| 4,632,561 | 12/1986 | Rosencwaig et al. | 356/432 |
| 4,636,088 | 1/1987 | Rosencwaig et al. | 374/5 |
| 4,679,946 | 7/1987 | Rosencwaig et al. | 374/5 |
| 4,710,030 | 12/1987 | Tauc et al. | 356/432 |
| 4,750,822 | 6/1988 | Rosencwaig et al. | 356/445 |
| 4,795,260 | 1/1989 | Schuur et al. | 356/400 |
| 4,854,710 | 8/1989 | Opsal et al. | 356/432 |
| 4,952,063 | 8/1990 | Opsal et al. | 356/432 |
| 4,999,014 | 3/1991 | Gold et al. | 356/382 |
| 5,042,951 | 8/1991 | Gold et al. | 356/369 |
| 5,042,952 | 8/1991 | Opsal et al. | 356/432 |
| 5,074,669 | 12/1991 | Opsal | 356/445 |

OTHER PUBLICATIONS

"Sound velocity and index of refraction of AlAs measured by picosecond ultrasonics", H.T. Grahn et al., Appl. Phys. Lett. 53 (21), 21 Nov. 1988.

"Elastic properties of silicon oxynitride films determined by picosecond acoustics", H.T. Grahn et al., Appl. Phys. Lett. 53 (23), 5 Dec. 1988.

"Noninvasive picosecond ultrasonic detection of ultrathin interfacial layers: CFx at the Al/Si interface", G. Tas et al., Appl. Phys. Lett. 61 (15), 12 Oct. 1992.

"Surface generation and detection of phonons by picosecond light pulses", C. Thomsen et al., Physical Review B., vol. 34, No. 6, 15 Sep. 1986.

"Detection of Thin Interfacial Layers By Picosecond Ultrasonics", G. Tas et al., Mat. Res. Soc. Symp. Proc. vol. 259, 1992. (no month available).

"Measurements of the Kapitza Conductance between Diamond and Several Metals", R. J. Stoner et al., Physical Review Letters, vol. 68, No. 10, Mar. 1992.

"Kapitza conductance and heat flow between solids at temperatures from 50 to 300K", R. J. Stoner et al., Physical Review B, vol. 48, No. 22, 1 Dec. 1993.

Primary Examiner—Frank G. Font
Assistant Examiner—Robert Kim
Attorney, Agent, or Firm—Perman & Green, LLP

[57] ABSTRACT

An optical heat generation and detection system generates a first non-destructive pulsed beam of electromagnetic radiation that is directed upon a sample containing at least one interface between similar or dissimilar materials. The first pulsed beam of electromagnetic radiation, a pump beam (21a), produces a non-uniform temperature change within the sample. A second non-destructive pulsed beam of electromagnetic radiation, a probe beam (21b), is also directed upon the sample. Physical and chemical properties of the materials, and of the interface, are measured by observing changes in a transient optical response of the sample to the probe beam, as revealed by a time dependence of changes in, by example, beam intensity, direction, or state of polarization. The system has increased sensitivity to interfacial properties including defects, contaminants, chemical reactions and delaminations, as compared to conventional non-destructive, non-contact techniques. One feature of this invention is a determination of a Kapitza resistance at the interface, and the correlation of the determined Kapitza resistance with a characteristic of the interface, such as roughness, delamination, the presence of contaminants, etc.

19 Claims, 16 Drawing Sheets

APPARATUS AND METHOD FOR CHARACTERIZING THIN FILM AND INTERFACES USING AN OPTICAL HEAT GENERATOR AND DETECTOR

STATEMENT OF GOVERNMENT RIGHTS

This invention was made with government support under grant number DE-FG02-ER45267 awarded by the Department of Energy, and grant number DMR-9121747 awarded by the National Science Foundation. The government has certain rights in the invention.

CLAIM OF PRIORITY FROM A COPENDING PROVISIONAL PATENT APPLICATION

Priority is herewith claimed under 35 U.S.C. §119(e) from copending Provisional Patent Application 60/010,295, filed Jan. 22, 1996, entitled "Apparatus and Method for Characterizing Thin Film and Interface Characteristics Using an Optical Heat Generator and Detector", by Humphrey J. Maris et al.

CROSS-REFERENCE TO A RELATED PATENT APPLICATION

This patent application is related to U.S. patent application Ser. No. 08/689,287, filed Aug. 6, 1996, entitled "Improved Optical Stress Generator and Detector", by Humphrey J. Maris and Robert J. Stoner.

FIELD OF THE INVENTION

This invention relates to a system for measuring the properties of thin films and interfaces between thin films, and particularly to a system which introduces heat pulses into a thin film and optically measures the change in the temperature of the thin film during the time in which the introduced heat diffuses through and leaves the thin film.

BACKGROUND OF THE INVENTION

Presently, the nondestructive evaluation of thin films and interfaces is of interest to manufacturers of electrical, optical and mechanical devices which employ thin films. In one nondestructive technique a radio frequency pulse is applied to a piezoelectric transducer mounted on a substrate between the transducer and the film to be studied. A stress pulse propagates through the substrate toward the film. At the boundary between the substrate and the film, part of the pulse is reflected back to the transducer. The remainder enters the film and is partially reflected at the opposite side to return through the substrate to the transducer. The pulses are converted into electrical signals, amplified electronically, and displayed on an oscilloscope. The time delay between the two pulses indicates the film thickness, if the sound velocity in the film is known, or indicates the sound velocity, if the film thickness is known. Relative amplitudes of the pulses provide information on the attenuation in the film or the quality of the bond between the film and the substrate.

The minimum thickness of films which can be measured and the sensitivity to film interface conditions using conventional ultrasonics is limited by the pulse length. The duration of the stress pulse is normally at least 0.1 µsec corresponding to a spatial length of at least $3 \times 10^{-2}$ cm for an acoustic velocity of $3 \times 10^5$ cm/sec. Unless the film is thicker than the length of the acoustic pulse, the pulses returning to the transducer will overlap in time. Even if pulses as short in duration as 0.001 µsec are used, the film thickness must be at least a few microns.

Another technique, acoustic microscopy, projects sound through a rod having a spherical lens at its tip. The tip is immersed in a liquid covering the film. Sound propagates through the liquid, reflects off the surface of the sample, and returns through the rod to the transducer. The amplitude of the signal returning to the transducer is measured while the sample is moved horizontally. The amplitudes are converted to a computer-generated photograph of the sample surface. Sample features below the surface are observed by raising the sample to bring the focal point beneath the surface. The lateral and vertical resolution of the acoustic microscope are approximately equal.

Resolution is greatest for the acoustic microscope when a very short wavelength is passed through the coupling liquid. This requires a liquid with a low sound velocity, such as liquid helium. An acoustic microscope using liquid helium can resolve surface features as small as 500 Angstroms, but only when the sample is cooled to 0.1 K.

Several additional techniques, not involving generation and detection of stress pulses, are available for measuring film thickness. Ellipsometers direct elliptically polarized light at a film sample and analyze the polarization state of the reflected light to determine film thickness with an accuracy of 3–10 Angstroms. The elliptically polarized light is resolved into two components having separate polarization orientations and a relative phase shift. Changes in polarization state, beam amplitudes, and phase of the two polarization components are observed after reflection.

The ellipsometer technique employs films which are reasonably transparent. Typically, at least 10% of the polarized radiation must pass through the film. The thickness of metal sample films thus cannot exceed a few hundred Angstroms.

Another technique uses a small stylus to mechanically measure film thickness. The stylus is moved across the surface of a substrate and, upon reaching the edge of a sample film, measures the difference in height between the substrate and the film. Accuracies of 10–100 Angstroms can be obtained. This method cannot be used if the film lacks a sharp, distinct edge, or is too soft in consistency to accurately support the stylus.

Another non-destructive method, based on Rutherford Scattering, measures the energy of backscattered helium ions. The lateral resolution of this method is poor.

Yet another technique uses resistance measurements to determine film thickness. For a material of known resistivity, the film thickness is determined by measuring the electrical resistance of the film. For films less than 1000 Angstroms, however, this method is of limited accuracy because the resistivity may be non-uniformly dependent on the film thickness.

In yet another technique, the change in the direction of a reflected light beam off a surface is studied when a stress pulse arrives at the surface. In a particular application, stress pulses are generated by a piezoelectric transducer on one side of a film to be studied. A laser beam focused onto the other side detects the stress pulses after they traverse the sample. This method is useful for film thicknesses greater than 10 microns.

A film may also be examined by striking a surface of the film with an intense optical pump beam to disrupt the film's surface. Rather than observe propagation of stress pulses, however, this method observes destructive excitation of the surface. The disruption, such as thermal melting, is observed by illuminating the site of impingement of the pump beam with an optical probe beam and measuring changes in intensity of the probe beam. The probe beam's intensity is altered by such destructive, disruptive effects as boiling of the film's surface, ejection of molten material, and subsequent cooling of the surface. See Downer, M. C.; Fork, R. L.; and Shank, C. V., "Imaging with Femtosecond Optical Pulses", Ultrafast Phenomena IV, Ed. D. H. Auston and K. B. Eisenthal (Spinger-Verlag, N.Y. 1984), pp. 106–110.

Other systems measure thickness, composition, or concentration of material by measuring absorption of suitably-chosen wavelengths of radiation. This method is generally applicable only if the film is on a transparent substrate.

In a nondestructive ultrasonic technique described in U.S. Pat. No. 4,710,030 (Tauc et al.), a very high frequency sound pulse is generated and detected by means of an ultrafast laser pulse. The sound pulse is used to probe an interface. The ultrasonic frequencies used in this technique typically are less than 1 THz, and the corresponding sonic wavelengths in typical materials are greater than several hundred Angstroms. It is equivalent to refer to the high frequency ultrasonic pulses generated in this technique as coherent longitudinal acoustic phonons.

In more detail, Tauc et al. teach the use of pump and probe beams having durations of 0.01 to 100 psec. These beams may impinge at the same location on a sample's surface, or the point of impingement of the probe beam may be shifted relative to the point of impingement of the pump beam. In one embodiment the film being measured can be translated in relation to the pump and probe beams. The probe beam may be transmitted or reflected by the sample. In a method taught by Tauc et al. the pump pulse has at least one wavelength for non-destructively generating a stress pulse in the sample. The probe pulse is guided to the sample to intercept the stress pulse, and the method further detects a change in optical constants induced by the stress pulse by measuring an intensity of the probe beam after it intercepts the stress pulse.

In one embodiment a distance between a mirror and a corner cube is varied to vary the delay between the impingement of the pump beam and the probe beam on the sample. In a further embodiment an opto-acoustically inactive film is studied by using an overlying film comprised of an opto-acoustically active medium, such as arsenic telluride. In another embodiment the quality of the bonding between a film and the substrate can be determined from a measurement of the reflection coefficient of the stress pulse at the boundary, and comparing the measured value to a theoretical value.

The methods and apparatus of Tauc et al. are not limited to simple films, but can be extended to obtaining information about layer thicknesses and interfaces in superlattices, multilayer thin-film structures, and other inhomogeneous films. Tauc et al. also provide for scanning the pump and probe beams over an area of the sample, as small as 1 micron by 1 micron, and plotting the change in intensity of the reflected or transmitted probe beam.

While well-suited for use in many measurement applications, it is an object of this invention to extend and enhance the teachings of Tauc et al.

It is known in the art that the thermal conduction through layered structures having one or more thin films depends on the thermal diffusivities of the film materials, and also on the thermal boundary resistance arising at the interfaces between the films. The thermal boundary resistance was first studied by Kapitza for interfaces between superfluid liquid helium and copper. It is now common to refer to the thermal boundary resistance between any two materials as the Kapitza resistance $R_K$. The Kapitza resistance is defined such that a heat current $\dot{Q}$, through an interface between two materials gives rise to a temperature drop $\Delta T$ across the interface equal to $R_K \dot{Q}$. The same heat current also gives rise to large thermal gradients in the materials adjacent to the interface. As a practical matter, the interfacial temperature drop is usually negligible in comparison to the temperature difference between the interface and points only a short distance into the adjacent materials. This distance may be typically only a few tens of Angstroms at room temperature.

One approach for measuring the Kapitza resistance is to create a sudden temperature difference $\Delta T$ across an interface, and then to allow the materials on the two sides of the interface to return to thermal equilibrium (i.e. $\Delta T=0$). For times less than a few nanoseconds the Kapitza resistance plays an observable role in the rate of thermal equilibration. Thereafter the rate is dominated by the rate of thermal diffusion in the material adjacent to the interface. In other words, $\Delta T$ becomes approximately zero long before the temperature returns to equilibrium throughout the sample. Therefore, to make a measurement of $R_K$ using a transient heating approach it is necessary to use a heat generator which can be switched on and off in a time significantly less than one nanosecond, and to use a temperature detector with a time resolution which is also significantly less than one nanosecond.

Measurements of the Kapitza resistance were reported by R. J. Stoner et al., and by R. J. Stoner and H. J. Maris in 1989 and 1993 for a variety of metal films deposited onto carefully prepared insulating substrates. Their technique used a subpicosecond laser pulse to heat the metal film, and a second subpicosecond laser pulse to measure the cooling of the film via the small change in its reflectivity caused by the heating. The Kapitza resistances so obtained for several metal-dielectric interfaces were compared with a theoretical model in which the interfaces were assumed to be microscopically ideal. No attempt was made to include the possible effects of interfacial imperfections, such as defects or contaminants, in the theoretical models used to analyze and model the results. Moreover, these papers also surveyed the temperature dependence of the Kapitza resistance for a variety of pairings of solids, and did not relate knowledge about conditions prevailing at a particular sample interface to the measured Kapitza resistance.

A similar technique was used by Tas et al. in 1992 to observe the cooling of thin aluminum films deposited onto substrates consisting of silicon wafers coated with a soft polymer ranging in thickness from zero to 20 Å. It was shown that the presence of the polymer films lowered the rate of cooling of the aluminum into the silicon. As a quantitative illustration of the effect of the polymer film on the cooling rate, as the polymer thickness was increased from zero to 20 Å, the film was treated as a Kapitza resistance. However, this was merely an expedient for grouping the three series resistances consisting of (i) the Kapitza resistance associated with the interface between the aluminum and polymer, (ii) the thermal resistance of the polymer film, and (iii) the Kapitza resistance associated with the interface between the polymer and silicon. No attempt was made to analyze the Kapitza resistance associated with the interface between the polymer and silicon, no attempt was made to analyze the Kapitza resistances themselves, nor to analyze the possible change in the thermal conductivity of the polymer films themselves with thickness. Moreover, the polymer was considered to be a uniform film having a definite thickness, and bulk physical properties. The Kapitza resistances obtained for the specimens in which the interfacial polymer layers was present were compared with a sample in which there was no polymer layer (i.e. aluminum on silicon); however, this comparison was made only to demonstrate that the effective thermal impedance associated with the polymer increased with the polymer thickness. No attempt was made to compare the reported Kapitza resistances with values obtained for a known perfect interface, nor with a theoretical model.

OBJECTS OF THE INVENTION

Therefore, it is an object of this invention to provide an improved noncontact and nondestructive method and apparatus for evaluating the condition of interfaces between one or more solids.

It is a further object of this invention to provide an improved method and apparatus for analyzing interfaces in which heat is deposited in a sample by partial absorption of a short radiation pulse.

It is a further object of this invention to provide an improved method and apparatus for detecting a change in the temperature of a sample using a radiation probe with a temporal resolution of much less than 1 nanosecond.

It is further object of the subject invention to provide a method and apparatus for evaluating interface conditions between two materials, wherein a change in a time dependent optical property, such as the intensity of a reflected radiation probe, is monitored as a function of time to study the flow of heat through a sample containing one or more interfaces, and to correlate the change in the monitored optical property with microscopic and other characteristics of the interface, such as surface roughness, and effective contact area and adhesion strength.

SUMMARY OF THE INVENTION

The foregoing and other problems are overcome and the objects of the invention are realized by methods and apparatus in accordance with embodiments of this invention.

This invention relates to a system and method for the characterization of thin films and interfaces between thin films through measurements of their mechanical and thermal properties. In the system and method a sample is provided which includes one or more thin films. In the system and method a measurement is made of at least one transient optical response of the sample to a pump pulse of optical radiation. The measured transient response or responses can include at least one of a measurement of a modulated change $\Delta R$ in an intensity of a reflected portion of a probe pulse, a change $\Delta T$ in an intensity of a transmitted portion of the probe pulse, a change $\Delta P$ in a polarization of the reflected probe pulse, a change $\Delta \phi$ in an optical phase of the reflected probe pulse, and a change in an angle of reflection $\Delta \beta$ of the probe pulse, each of which may be considered as a change in a characteristic of a reflected or transmitted portion of the probe pulse. The measured transient response or responses are then analyzed and the measured transient response or responses are used to give information about the ultrasonic waves that are produced in the structure, and information regarding the heat that flows from one part of the structure to another part.

The information that is obtained from the use of the measurement methods and apparatus of this invention can include: (a) a determination of the thickness of thin films with a speed and accuracy that is improved compared to earlier methods; (b) a determination of the thermal, elastic, and optical properties of thin films; (c) a determination of the stress in thin films; and (d) a characterization of the properties of interfaces, including the presence of roughness and defects. This latter feature is of most concern to the teaching of this invention, wherein the characterization of the interface properties is preferably obtained by determining the Kapitza resistance of the interface(s), and then comparing the determined Kapitza resistance with data obtained from a reference interface, and/or from one or more simulations of the interface made with suitable modelling techniques. In this regard the interface simulations can be iterated by varying interface properties, such as by modelling the presence of contaminants, delamination, roughness, etc., until the modelled interface characteristics converge with the determined Kapitza resistance data.

This invention results from the realization that a truly effective instrument for measuring the properties of a sample containing one or more interfaces between two solids can be achieved by optically generating a sudden temperature difference across an interface, and by making a time-resolved measurement of the change in the optical response of the sample to the probe pulse.

One aspect of this invention is a technique which in some ways is analogous to the optical method of Tauc et al., but which employs heat flow across one or more interfaces or films to investigate their properties. It is equivalent to refer to the flow of heat in this new technique as a flow of incoherent thermal phonons. Unlike the method of Tauc et al., it is a feature of the present invention that the thermal phonons employed may include all possible phonon frequencies and polarizations which can exist in a subject material, according to the principles of quantum mechanics. Such frequencies may extend to 10 THz ($10 \times 10^{12}$ Hz) or greater in many materials, and the corresponding phonon wavelengths can be accordingly much shorter than those employed in the Tauc et al. method. In the present invention the flow of thermal phonons across ore or more interfaces between two or more materials is monitored to yield information about the characteristics of the interface(s). The higher frequency phonons employed in this technique give greater sensitivity to interfacial features than can be achieved in previous techniques.

In accordance with a further aspect of this invention, the Kapitza resistance is measured by focusing a very short duration laser pulse, a pump pulse, onto a sample consisting of one or more thin films. In the simplest case this sample consists of a single film which is thick compared to the optical absorption length at the laser wavelength. Partial absorption of the laser pulse in the film gives rise to a sudden increase in the film's temperature of, typically, less than about 50 K. This temperature rise is accompanied by a small change in the transient optical response of the film, wherein a change in the transient optical response is proportional to the temperature change. The heated film is then allowed to cool with no further heating for up to 10 nanoseconds, during which time its temperature is monitored by measuring the change in the reflected intensity of a second laser beam, or probe beam, that is directed onto or closely adjacent to the heated region. In this manner a record is made of the optical response of the heated region as a function of time. By carrying out an analysis of the time dependence of the cooling of the film, information about thermal transport in the sample, including the Kapitza resistance at one or more interfaces, may be obtained.

It is of particular significance in regard to the present invention that the Kapitza resistances so obtained may be modified by the microscopic characteristics of the interface, such as roughness. It is a feature of the present invention that a system and method is disclosed which relates measured Kapitza resistances to the microscopic characteristics of interfaces between two solids.

The invention features an optical generation and detection system for non-destructively measuring the properties of one or more interfaces within a sample. There is a radiation source for providing a pump beam having short duration radiation pulses having an intensity and at least one wavelength selected to non-destructively and non-uniformly raise the temperature of the sample, a radiation source for providing a probe beam, a mechanism for directing the pump beam to the sample to generate a change in the temperature within the sample, and a mechanism for guiding the probe beam to a location at the sample to intercept the region in which the temperature was changed by the pump beam. A suitable optical detector is provided that is responsive to a reflected portion of the probe beam for detecting the change in the optical constants and/or thermal expansion within the sample induced by the change in its temperature.

In one embodiment, the optical detector measures the intensity of the reflected or transmitted probe beam. The pump and probe beam may be derived from the same source that generates a plurality of short duration pulses, and the system further includes a beam splitter for directing a first portion of the source beam to form the pump beam, having the plurality of pulses, and directing a second portion to form the probe beam, also having the plurality of pulses. The source beam has a single direction of polarization and the system further includes means for rotating the polarization of the probe beam and a device, disposed between a sample and the optical detector, for transmitting only radiation having the rotated direction of polarization. The temperature detector may further include a chopper for modulating the pump beam at a predetermined frequency. The system can further include a mechanism for establishing a predetermined time delay between the impingement of a pulse of the pump beam and a pulse of the probe beam upon the sample. The system can further include circuitry for averaging the output of the optical detector for a plurality of pulse detections while the delay between impingements remains set at the predetermined time delay. The delay setting mechanism may sequentially change the predetermined time delay and the circuitry for averaging may successively average the output of the optical detector during each successive predetermined time delay setting.

By example, the pump beam may receive 1% to 99% of the source beam, and the source beam may have an average power of 10 µW to 10 kW. The source beam may include wavelengths from 100 Angstroms to 100 microns, and the radiation pulses of the source beam may have a duration of 0.01 picosecond to 1 nanosecond.

The sample may include a substrate and at least one thin film to be examined disposed on the substrate such that interfaces exist where the films meet, and/or where the film and the substrate meet. For a sample with an optically opaque substrate, at the pump wavelength, the pump and probe beams may both impinge from the film side, or the pump may impinge from the film side and the probe may impinge from the substrate side. For a sample with a transparent substrate, both beams may impinge from the film side, or from the substrate side, or from opposite sides of the sample. The optical and thermal constants of the films and substrate are such that the pump pulse changes the temperature within at least one film with respect to the substrate. The temperature within one or more of the thin films disposed on the substrate may be uniform, and may be equal in several films. The films may have thicknesses ranging from about 1 Å to about 100 microns. At least one film in the sample has the property that when its temperature changes it causes at least one of a change $\Delta R$ in an intensity of a reflected portion of a probe pulse, a change $\Delta T$ in an intensity of a transmitted portion of the probe pulse, a change $\Delta P$ in a polarization of the reflected probe pulse, a change $\Delta\phi$ in an optical phase of the reflected probe pulse, and a change in an angle of reflection $\Delta\beta$ of the probe pulse. The probe beam source may provide a continuous radiation beam, and the pump beam source may provide at least one discrete pump pulse having a duration of 0.01 to 100 psec and an average power of 10 µW to 1 kW. Alternatively the probe beam source may provide probe beam pulses having a duration of 0.01 to 100 psec, the pump beam and probe beam may impinge at the same location on the sample, and the mechanisms for directing and guiding may include a common lens system for focusing the pump beam and the probe beam onto the sample. The position of impingement of the probe beam may be shifted spatially relative to that of the pump beam, and the probe beam may be transmitted or reflected by the sample.

One or more fiber optic elements may be incorporated within the system. Such fibers may used to guide one or more beams within the system for reducing the size of the system, and/or to achieve a desired optical effect such as focussing of one or more beams onto the surface of the sample. To achieve focussing, the fiber may be tapered, or may incorporate a small lens at its output. A similar focussing fiber can be used to gather reflected probe light and direct it to an optical detector.

This invention also teaches a method for optically and non-destructively generating and detecting a temperature change in a test sample, including steps of producing a pump beam having at least one wavelength selected to non-destructively generate a non-uniform temperature change in the sample, producing a probe radiation beam, directing the pump beam to a surface of the sample to generate a non-uniform temperature change, and guiding the probe beam to a location at the sample to intercept the temperature change. The method further includes a step of detecting the change in the sample induced by the non-uniform temperature change by measuring the change in the optical response of the sample to the probe beam.

Also disclosed is a method that includes the steps of producing a source beam having short duration pulses of radiation, diverting a first portion of the source beam to form a pump beam having an intensity and at least one wavelength selected to non-destructively generate a non-uniform temperature change within the sample, diverting a second portion of the source beam to form a probe beam and directing the probe beam to a location on the sample to intercept the temperature change, and detecting the change in the sample induced by the temperature change by monitoring the probe beam after it impinges on the sample.

BRIEF DESCRIPTION OF THE DRAWINGS

The above set forth and other features of the invention are made more apparent in the ensuing Detailed Description of the Invention when read in conjunction with the attached Drawings, wherein:

FIG. 4b is block diagram that illustrates an embodiment of electro-optical components responsive to the delay between the pump and probe pulses, as shown in FIG. 4a;

DETAILED DESCRIPTION OF THE INVENTION

The teaching of this invention is embodied by an optical generator and detector of a non-uniform temperature change within a sample, hereinafter sometimes referred to as an optical heat generation and detection system. In this system a first non-destructive pulsed beam of electromagnetic radiation is directed upon a sample containing at least one interface between similar or dissimilar materials. The first pulsed beam of electromagnetic radiation, referred to herein as a pump beam 21a, produces a non-uniform temperature change within the sample. A second non-destructive pulsed beam of electromagnetic radiation, referred to herein as a probe beam 21b, is directed upon the sample such that at least one of the polarization, direction and intensity of a reflected portion of the probe beam 21b' or a transmitted portion of the probe beam 21b" is affected by a change in the optical constants of the materials comprising the sample, or by a thermal expansion within the sample resulting from the non-uniform change in its temperature. Physical and chemical properties of the materials, and of the interface, are measured by observing the changes in the reflected or transmitted probe beam intensity, direction, or state of polarization as revealed by the time dependence of the changes in beam intensity, direction or state of polarization. An optical heat generation and detection system of this type can have dramatically increased sensitivity to interfacial properties including defects, contaminants, chemical reactions and delaminations, as compared to conventional non-destructive, non-contact techniques. The very short time scale is particularly important for achieving the high sensitivity to interfacial properties, and for measuring the properties of films having thicknesses less than several microns.

One feature of this invention is a determination of a Kapitza resistance at the interface, and the correlation of the Kapitza resistance with a characteristic of the interface, such as roughness, delamination, the presence of contaminants, etc.

Figure 10:
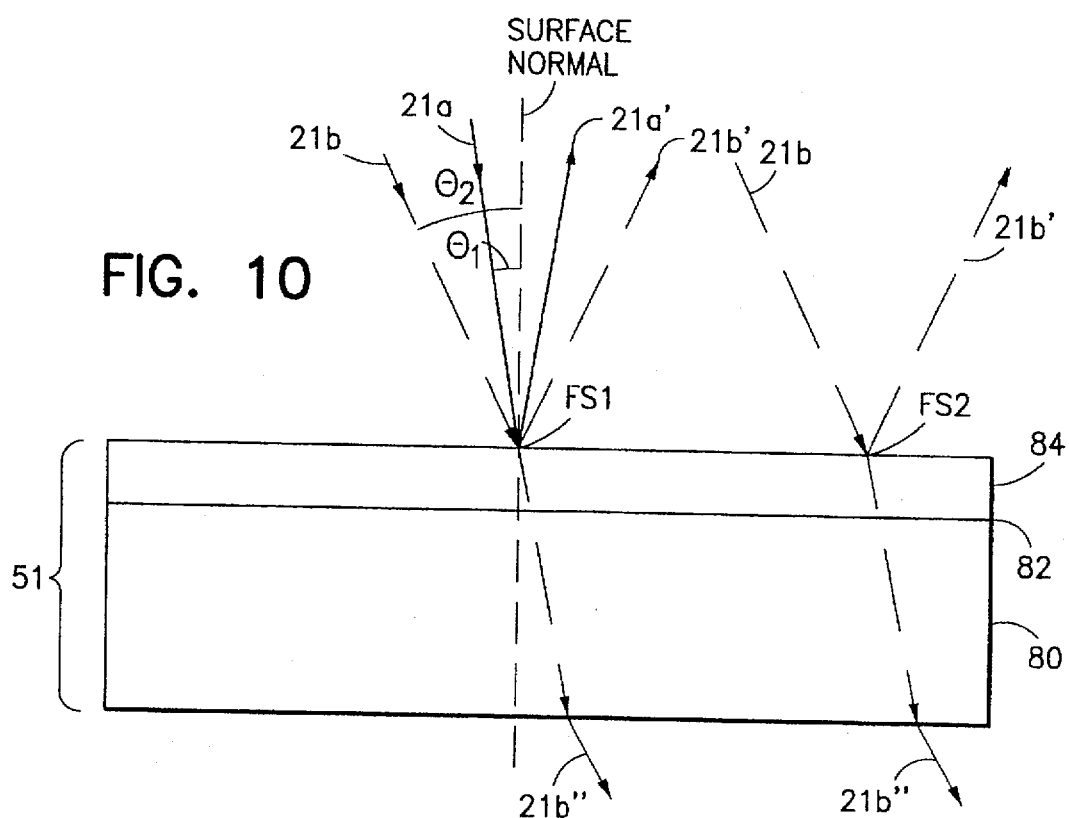
FIG. 10 is a cross-sectional, enlarged view of the sample having the substrate, thin film layer, and the interface between the substrate and the thin film layer, and that further illustrates the impingement of the probe beam within a focussed spot (FS1) of the pump beam, and the impingement of the probe beam at a second FS (FS2) that is displaced from FS1.

By way of introduction, the arrangement of the pump and probe beam according to this invention is illustrated in FIG. 10. A test sample 51 is shown comprised of a film 84 disposed on substrate 80. An interface 82 is formed between the film 84 and the substrate 80. By example, the substrate 80 may be comprised of a semiconductor such as silicon and may form a portion of a semiconductor wafer, and the film 84 may be an overlying layer of oxide, polymer, metal, or another semiconductor. To test the sample 51 the pump beam 21a is directed onto a position on the film 84 (referred to as a focal spot FS1) to generate a non-uniform temperature in the sample due to the absorption of energy in the film 84 and substrate 80 from pump pulses in the pump beam. The pump beam 21a is incident on the sample 51 at an angle $\theta_1$ offset from normal. A portion of the pulsed pump beam is absorbed in the film and substrate thereby causing a transient, localized heating effect. The unabsorbed portion is reflected as the reflected pump beam 21a'. The probe beam 21b may be directed to the same spot (FS1) on the sample at an angle $\theta_2$ to intercept the energy deposited by the pump beam 21a. In other embodiments of the invention the probe beam 21b can be directed to another location (FS2). A portion of the probe beam 21b reflects from the film 84 as the reflected probe beam 21b'. Any portion of the probe beam 21b that is transmitted through the sample is referred to as the transmitted probe beam 21b". The actual values of angles $\theta_1$ and $\theta_2$ can be selected from a wide range of angles. The intensities of the reflected and transmitted pump and probe beams depend on the optical constants of the film 84 and substrate 80. FIG. 10 also illustrates probing at points (FS2) at a distance from the pump beam FS1, which is a further embodiment of this invention.

The non-uniform temperature induced in the sample 51 corresponds to a non-uniform distribution of thermal energy. Under typical conditions, this energy is initially imparted to electronic carriers in the sample 51 by the pulsed pump beam 21a. Electronic carriers may include electrons and holes if the film 84 or substrate 80 is a semiconductor, and may include electrons if the film 84 is a metal. Under typical conditions the film 84 is a metal, the substrate 80 is an insulator such as Si or glass, and the film 84 absorbs a pump radiation pulse within several hundred Angstroms of the surface of the sample. Within a period of time lasting several picoseconds, the excited electrons diffuse and transfer the energy deposited by the pump pulse 21a to thermal phonons in the film 84. The distance over which the excited electrons diffuse before a state of equilibrium between the thermal phonons and electrons is reached may be much greater than the penetration depth of the pump light into the film 84. As a result of the rise in the temperature of the film 84, a stress pulse is also generated or launched in the sample 51. The stress pulse propagates with a velocity $v_s$ given by the speed of sound in the medium through which it propagates. By example, the speed of sound in glass is approximately 60 Å/psec, and the speed of sound in silicon is approximately 84 Å/psec.

Figures 11A, 11B, 11C:
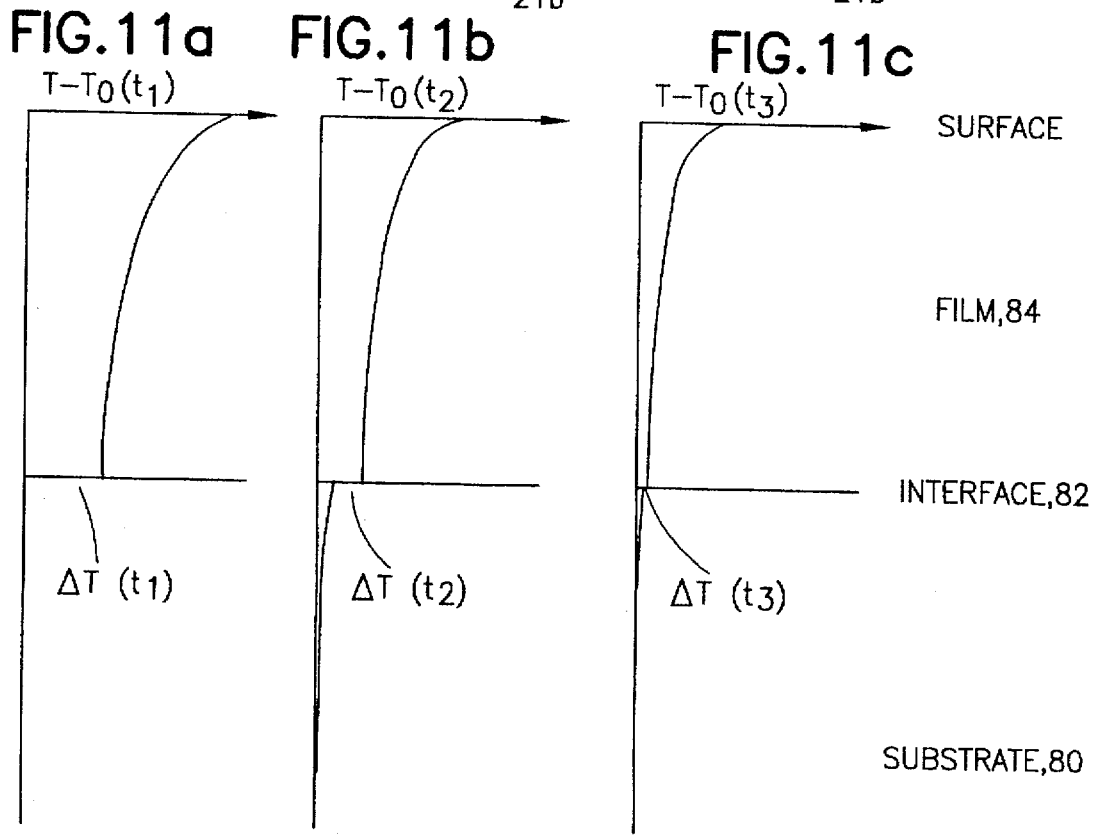
FIGS. 11a, 11b, 11c are graphs illustrating a change with time in a temperature differential across the interface between the substrate and the thin film.

The non-uniform temperature change along a line normal to the sample, illustrated in FIGS. 11a–11c, is for a sample containing a metal film with an optical absorption length, at the pump wavelength, that is short compared to the thickness of the film 84, and a substrate 80 which is an insulator. FIGS. 11a–11c show the time evolution of the heat deposited by a pump pulse within a simple (thin film/transparent substrate) sample. $\Delta T$ is initially at a maximum as no heat is deposited in the substrate 80. At later times, (FIGS. 11b and 11c) as heat flows across the interface 82 into the substrate 80 $\Delta T$ diminishes. In this figure, the temperature prior to the absorption of the pump pulse is $T_0$ and the temperature increase due to the pump pulse is $T-T_0$. Curve (a) shows the temperature along the direction of the surface normal at a time $t_1$ several picoseconds after the absorption of a pump pulse in the film, when the excited electrons and thermal phonons have reached thermal equilibrium. The temperature difference between the substrate 80 and the film 84 is $\Delta T_1$ and the rate of energy transfer from the film to the substrate is $\dot{Q}$, which may be written in terms of the Kapitza resistance $R_\kappa$ as follows: $\Delta T_1/R_\kappa$. Curve (b) shows the temperature in the film 84 and substrate 80 at a later time $t_2$ when some of the thermal energy has entered the substrate. The temperature difference between the substrate 80 and the film 84 is $\Delta T_2$ and the rate of energy transfer from the film 84 to the substrate 80 is $\dot{Q}$. This may be written in terms of the Kapitza resistance $R_\kappa$ as follows: $\Delta T_2/R_\kappa$. Curve (c) shows the temperature in the film 84 and substrate 80 after a time such that the temperature difference between the substrate and the film is approximately zero. The time for the condition of zero temperature difference across the interface 82 to be reached, under typical conditions, is much less than 100 nanoseconds. The value of $R_\kappa$ thus has a large effect on the rate of change of the temperature within the substrate 80 and the film 84.

The flow of heat in materials is governed by the following equation:

$$\frac{\partial T(\vec{r},t)}{\partial t} = \frac{\sigma}{C} \nabla^2 T(\vec{r},t) \tag{1}$$

In Equation (1) $\sigma$ is the thermal conductivity and C is the specific heat. In equilibrium the temperature is uniform and constant throughout the structure and is equal to $T_0$, and $T(\vec{r}, t)=T_0+\Delta T(\vec{r}, t)$, where $\Delta T(\vec{r}, t)$ is the temperature change associated with the energy deposited by the pump beam 21a in the structure.

The flow of heat across an interface having a Kapitza resistance $R_\kappa$ from side A, having temperature $T_A$, to side B, having temperature $T_B$, is governed by the following equation:

$$\dot{Q}_{int}(t) = \frac{1}{R_K}(T_A(t) - T_B(t)) \tag{2}$$

In order to calculate the flow of heat subject to specified initial conditions within a particular structure it is necessary to solve Eq. (1) at all points in the structure subject to appropriate boundary conditions. At interfaces between adjacent materials Eq. (2) must be satisfied.

For the illustrative case in which the structure contains a thin film of thickness $d_{film}$ and specific heat $C_{film}$ that is deposited on a thick substrate with high thermal conductivity, Eqs. (1) and (2) have the approximate analytical solution:

$$\Delta T_{film}(t)=\Delta T_{film}(t=0)\exp(-t/\tau) \tag{3}$$

where $\tau=R_\kappa C_{film}d_{film}$. Typical values for a 200 Å thick aluminum film on a diamond substrate are $R_\kappa=5\times10^{-5} cm^2 K/W$ and $C_{film}=2.5$ W/cm$^3$K. These values give $\tau \simeq 250$ psec. Therefore the temperatures in the film 84 and substrate 80 adjacent to the interface 82 become approximately equal in a time much less than one nanosecond.

The temperature change in the aluminum film gives rise to a small proportional change in the reflectivity of the sample 51. As such, a curve of the reflectivity change versus time acquired in the manner described above, for times less than a few nanoseconds, is equivalent to a curve of the temperature change versus time. From the observed rate of change of the temperature, and known values of the film thickness and specific heat, the Kapitza resistance of the film/substrate (or film/film) interface 82 may be obtained.

To obtain a measure of the characteristics or quality of the interface 82 it is preferred to then compare the measured value of $R_\kappa$ with a previously measured value for a known, high quality reference interface between the materials of interest, and/or with a calculated theoretical value obtained from a simulation of the sample's structure.

That is, having determined the Kapitza resistance at the film/substrate interface it is then possible, in accordance with this invention, to compare the value to a known value for a reference interface and/or with a calculated value. If a difference exists it is then possible to iteratively simulate different interface conditions and characteristics so as to determine an actual, non-ideal interface characteristic, such as the presence of roughness at the interface, or the presence of a further interface resulting from a reaction between the film and the substrate, or the presence of a delamination between the film and the substrate.

In accordance with an aspect of this invention, the physical properties of the sample 51 which may be determined in this manner include properties which may affect the time dependence of Kapitza resistance-related signals and/or their amplitudes. These are (among others) layer thicknesses, sound velocities, interfacial roughness, interfacial adhesion strength, thermal diffusivities, stress, optical constants, surface roughness, and interfacial contaminants.

Figure 21:
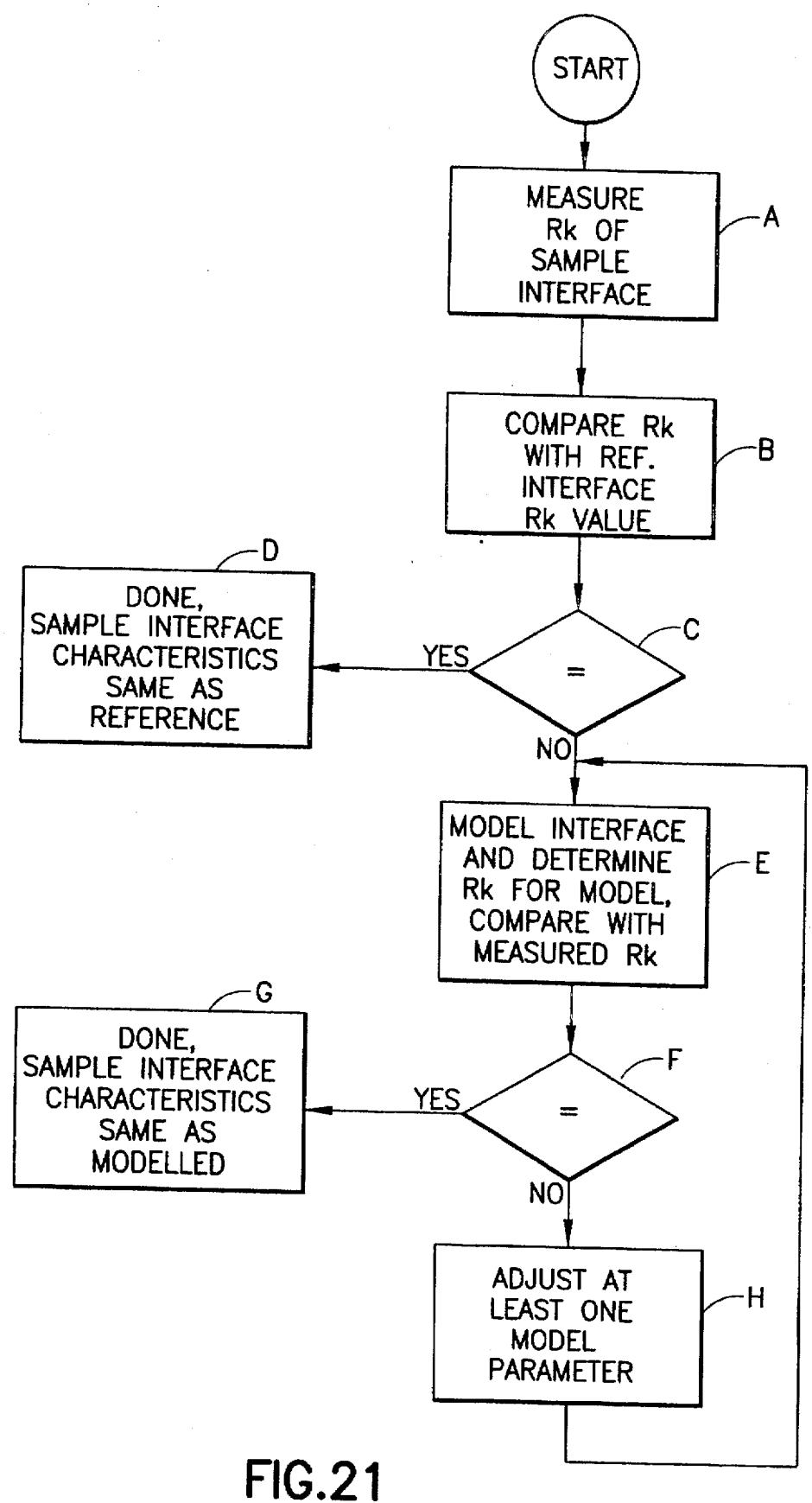
FIG. 21 is a logic flow diagram that illustrates a simulation method in accordance with an aspect of this invention.

Referring to FIG. 21, the logic flow diagram illustrates one embodiment of a method of this invention. At Block A the system is used to measure the Kapitza resistance ($R_\kappa$) of the sample's interface 82. At Block B the measured value is compared with a value of $R_\kappa$ obtained for a reference "known good" interface. If they are equal (Block C), control passes to Block D, where the sample's interface characteristics are declared to be equivalent to the reference interface characteristics (e.g., to have a known amount of smoothness, a known concentration of contaminants, etc.). If the test at Block C fails, the interface may be modelled at Block E and a calculated value of $R_\kappa$ for the modelled interface is compared with the measured value. The modelling may be a step-wise process that operates in picosecond or less increments of time. If the calculated value of $R_\kappa$ for the modelled interface is equal to the measured value (Block F), the sample's interface characteristics are declared to be the same as those used in the model. If the test at Block F fails, control passes to Block H where at least one interface parameter or characteristic is varied (e.g., roughness), and control then passes back to Block E to model the revised interface and to determine the value of $R_\kappa$ for the revised interface. This procedure can continue in this manner until the measured value of $R_\kappa$ is found to fall within an acceptable range of values about the calculated value of $R_\kappa$, at which time the sample's interface characteristics are declared to be the same as or similar to those of the model at this point in the iterative modelling process. That is, the interface simulations can be iterated by varying interface properties, such as the presence and concentration of contaminants, delamination, roughness, etc., until the modelled interface characteristics converge with the determined Kapitza resistance data.

It should be noted that in some embodiments Blocks B, C and D can be eliminated, and the determination of one or more interface characteristics determined solely in accordance with simulated interface data. In other embodiments Blocks E–G can be eliminated, and the measured Kapitza resistance compared instead with values obtained from a plurality of reference interfaces, such as interfaces having known degrees of surface roughness, delaminations, contaminants, etc.

An aspect of this invention is thus a method for characterizing a sample, the sample having an interface between a substrate and at least one structure that is an intentionally or a non-intentionally formed layer or body that is disposed upon or within the substrate. The method includes a first step of (A) generating a reference data set of a transient optical response of the sample to an optical pump pulse, the reference data set being generated from at least one of (a) at least one reference sample or (b) a simulation of an interfacial thermal response of a simulated sample. The method includes further steps of (B) applying a sequence of optical pump pulses and optical probe pulses to the sample; (C) comparing a measured transient response of the sample to the reference data set; (D) adjusting a value of the one or more characteristics of the sample so as to bring the reference data set into agreement with the measured transient response; and (E) associating the adjusted value of the one or more characteristics with a value of one or more actual characteristics of the structure, wherein at least one of the actual characteristics is a Kapitza resistance of the interface. The method includes a further step of (F) correlating the actual Kapitza resistance with microscopic and other properties of the interface, such as the presence or absence of roughness, delaminations, defects, contaminants, adhesion, impurities, and the presence of undesirable interlayers.

The foregoing example of Equation 3 assumes that heat diffuses throughout the film rapidly, and that the temperature in the film 84 remains uniform. It further assumes that heat entering the substrate 80 rapidly diffuses away, so that the temperature rise in the substrate is much smaller than the initial temperature rise in the film 84. For structures in which these conditions are not satisfied (for example because the thermal conductivities of the substrate or film are too low, or because the thickness of the film is too great, or because the structure is too complicated) Equations 1 and 2 must be solved numerically for $\Delta T(\vec{r}, t)$ throughout the structure for a particular set of parameters. In the manner described below $\Delta T(\vec{r}, t)$ may be related to the observed reflectivity change $\Delta R(t)$ or transmission change $\Delta T(t)$. The Kapitza resistance of one or more interfaces may be determined by finding values which give a computed $\Delta R(t)$ or $\Delta T(t)$ that most closely resembles the observed results. To determine the quality of any one of these interfaces, the corresponding value of the Kapitza resistance is preferably compared with a previously measured value for a high quality interface, or with a value obtained from a theoretical model of the film/substrate system, as described above.

The reflectivity change $\Delta R(t)$ in a structure due to a temperature change $\Delta T(\vec{r}, t)$ may be written as follows:

$$\Delta R(t) = \int \Delta T(\vec{r}, t) f(\vec{r}) d\vec{r} \qquad (4)$$

In this equation $f(\vec{r})$ is the change in the reflectivity associated with a small temperature change at position $\vec{r}$.

This function may be determined for any structure by solving the classical equations of optics for the reflectivity of the structure at two closely spaced temperatures. To make a precise numerical calculation it is necessary to know how the optical constants of the materials in the structure vary with temperature, in addition to the thermal coefficients of expansion of the materials. These parameters are typically known or can be determined for most film/substrate systems.

Figure 1A:
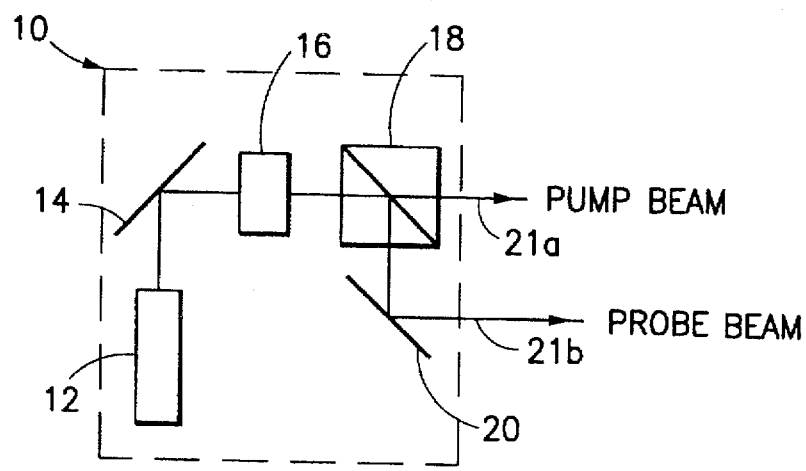
FIGS. 1a, 1b, 1c depict embodiments of optical sources for use with the system of this invention.
Figure 1B:
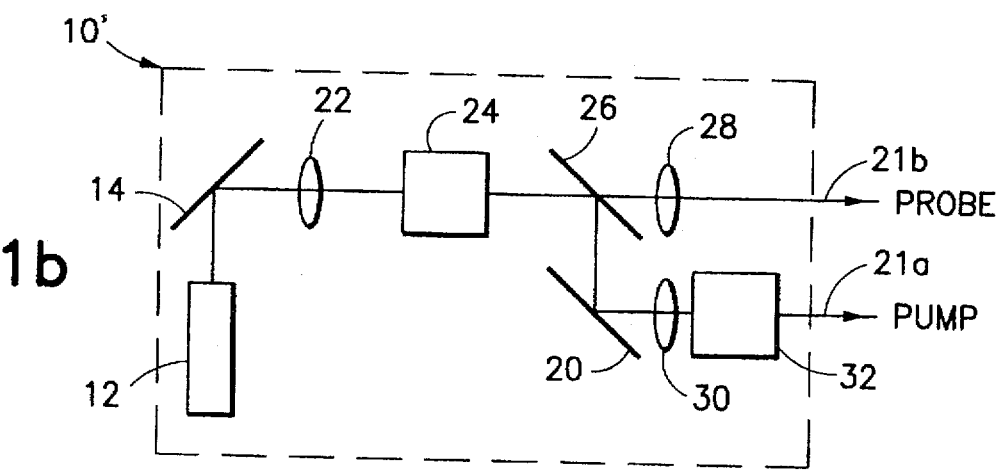
Figure 1C:
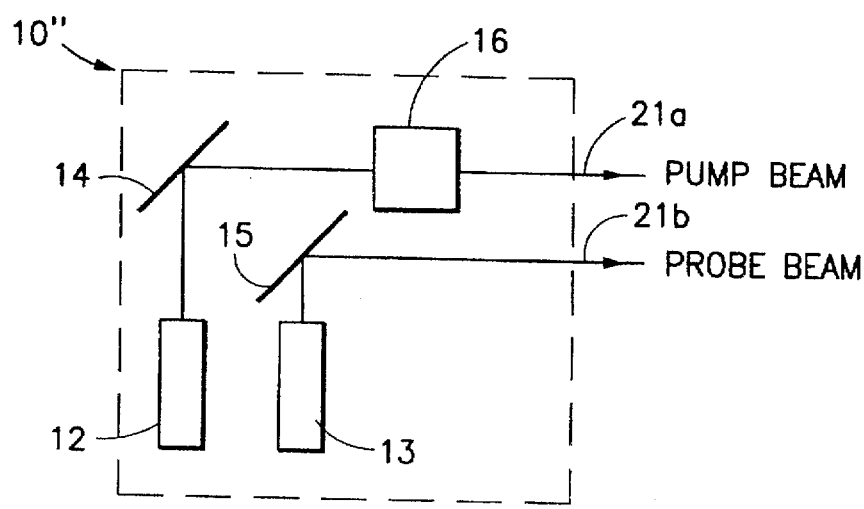
Figure 2:
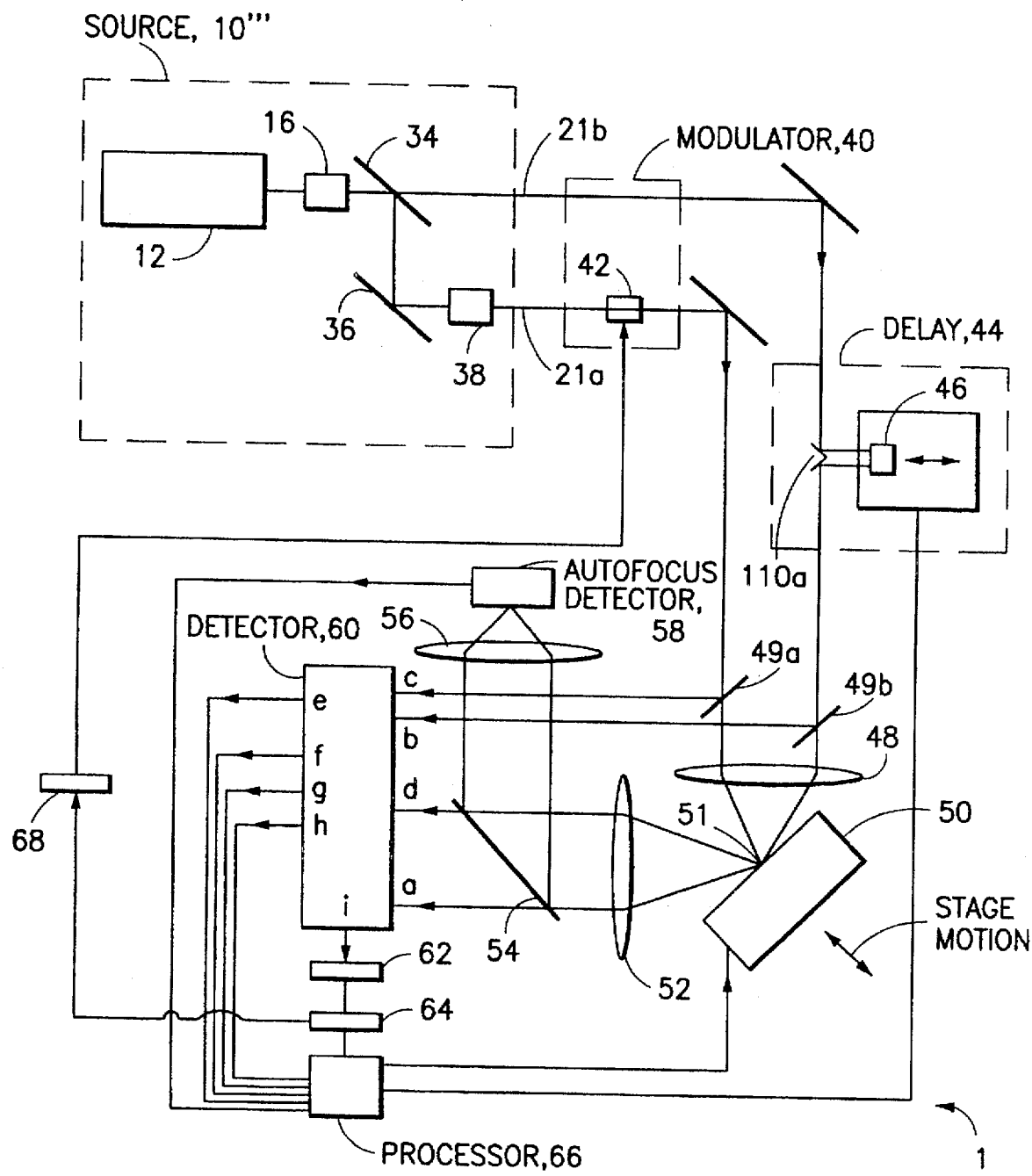
FIG. 2 is a block diagram of an embodiment of a sample characterization system in accordance with this invention.

FIGS. 1a–1c illustrate various embodiments of optical sources that are suitable for practicing this invention, while FIG. 2 is a block diagram of an optical generation and detection system for performing non-destructive picosecond time-scale thin film and interface characterizations, referred to hereinafter as system 1.

A first embodiment of an optical source 10 is shown in FIG. 1a, in which the beam from a laser 12 is reflected from a mirror 14 and passes through a polarization rotating device, such as a half-wave plate 16, to a polarizing beam splitter 18. The beams emerging from the polarizing beam splitter 18 are orthogonally polarized, and the ratio of their intensities may be varied through a wide range by adjusting the orientation of the half-wave plate 16. One beam forms the pump beam 21a, while the probe beam 21b reflects from a mirror 20.

An alternative embodiment of an optical source 10' shown in FIG. 1b includes a frequency doubling crystal 24, such as BBO or LBO, onto which the laser light is focused by a lens 22 positioned between it and the laser 12. The coaxial beams of light emerging from the frequency doubling crystal 24 are separated by means of a dichroic mirror 26 into the pump and probe beams, each of which is then collimated by lenses 28 and 30. The polarization of the pump beam 21a is rotated to be perpendicular to that of the probe beam 21b by means of a half-wave plate 32. The dichroic mirror 26 may be chosen to pass the fundamental frequency of the laser 12 and reflect the second harmonic, giving a probe beam at the fundamental and a pump beam at the second harmonic. Alternatively, the dichroic mirror 26 may be chosen to pass the second harmonic and reflect the fundamental, giving the probe beam 21b at the second harmonic and the pump beam 21a at the fundamental, as shown in FIG. 1b.

Figure 4A:
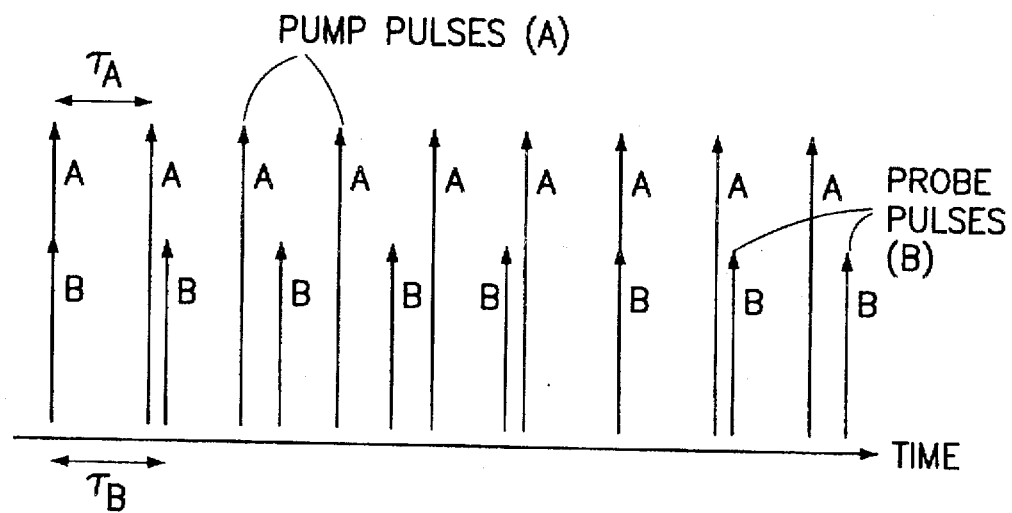
FIG. 4a is a diagram that illustrates a variability in a temporal offset between pump and probe beam pulses.

Another embodiment of an optical source 10" is shown in FIG. 1c, in which the pump and probe beams are produced by two different lasers 12 and 13. In one embodiment, these may be identical pulsed lasers, in which case the upper beam is passed through the half-wave plate 16 to rotate its polarization relative to that of the lower beam by 90 degrees. Alternatively, the lasers 12 and 13 may emit dissimilar wavelengths (two "colors"). Alternatively, the probe laser 13 may emit a continuous (i.e. non-pulsed) beam. Alternatively, the pump laser 12 may emit pulses with a repetition period of $\tau_A$ and the probe laser 13 may emit pulses with a repetition period $\tau_B$, as shown in FIG. 4a. Such a scheme may be used to effect a continuously variable delay between the pump and probe pulses without the use of a mechanical delay stage 44 of a type depicted in FIG. 2.

Figure 4B:
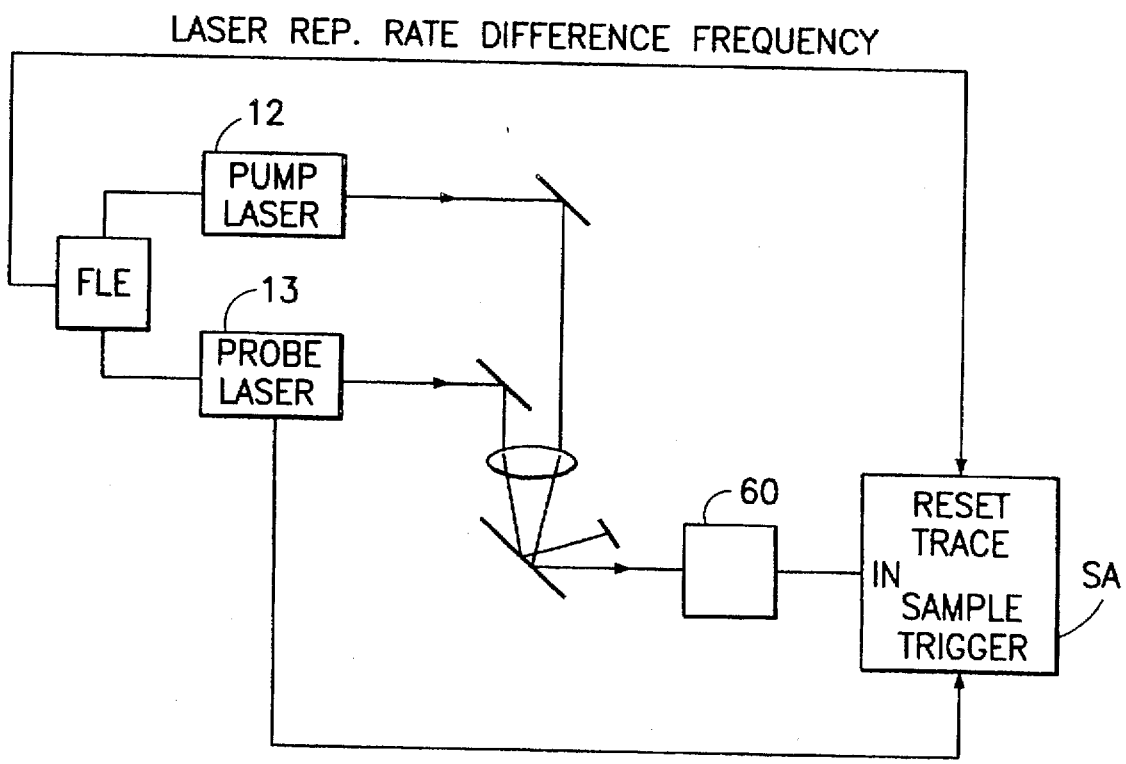

Referring now to FIG. 4b, in this alternative technique the delay between pairs of A and B pulses increases by a time $\tau_B - \tau_A$ from one repetition to the next. By example, $\tau_B - \tau_A$ may be 0.1 psec on average, and the repetition rate of the pump laser 12 may be 100 MHz. This gives a time between simultaneous arrivals of the pump and probe pulses of one millisecond (i.e., the scan time). This embodiment further includes suitable frequency locking electronics (FLE), mirrors, a lens, a suitable detector 60, and a fast signal averager (SA). A measurement of, by example, $\Delta R(t)$ may be performed by applying a signal corresponding to the reflected probe intensity from the output of the detector 60 to the input of the fast signal averager (SA), and by triggering sample acquisitions at times corresponding to the pulsing of the probe laser 13. A large number (e.g., thousands) of measurements may be averaged in order to effect a desired signal to noise ratio. It should be noted in regard to this invention that the delay stage and modulator described previously in regard to FIG. 2 may be omitted. It should also be appreciated that any "jitter" in the pulsing of the two lasers may have the effect of averaging the signals corresponding to closely spaced delay times, and that this effect may somewhat attenuate the high frequency components of the measurement.

Although the pump and probe lasers are depicted in FIG. 1c separately, they may have one or more optical elements in common, including the gain medium. Other permutations of pump and probe color, polarization and pulse rate suggested by the above description may be used to achieve an improvement in signal quality, depending on the properties of the materials to be investigated.

Examples of the pulsed lasers suitable for use in the system 1 include an Argon ion pumped solid state mode-locked laser, such as Coherent Inc. Inova (Argon) and Mira (Ti:sapphire); a diode laser pumped solid state mode locked laser, such as a continuous wave diode pumped frequency doubled YAG and modelocked Ti:sapphire laser; and a direct diode pumped mode-locked solid state laser.

Referring to the embodiment of FIG. 2, a further embodiment of an optical source 10''' provides both the pump and probe beams 21a and 21b, respectively, in a manner similar to the embodiment of FIG. 1a. In the FIG. 2 arrangement the linearly polarized beam from laser 12 passes through the half-wave plate 16, which is used to rotate its polarization. The polarized beam is then split into pump and probe beams by a dielectric beam splitter 34. The ratio of pump to probe may be varied by rotating the incoming polarization. The lower beam is the pump beam 21a, and the upper beam is the probe beam 21b. The pump beam 21a passes through a half-wave plate/polarizer combination 38 which rotates its polarization to be orthogonal to that of the probe beam 21b, and which also suppresses any light not polarized along this orthogonal axis.

The pump and probe beams 21a and 21b are emitted by the source, and the intensity of the pump beam is modulated at a rate of about 1 MHz by an acousto-optic modulator (AOM) 40, or by a photoelastic modulator followed by a polarizer, or by other intensity modulation means. The probe beam path length is varied by translating a retroreflector 46 mounted on a computer-controlled delay stage 44, via a steering mirror combination 110a. Both beams are then focused by lens 48 onto the sample 51 mounted on a translatable sample stage 50, and are detected by a photodetector 60. In this embodiment the inputs to the detector 60 include portions of the input pump and probe beams (inputs c and b, respectively, via beam splitters 49a and 49b, respectively); and also include portions of the reflected pump beam 21a' and reflected probe beam 21b' (inputs d and a, respectively). Outputs from the detector 60 include signals proportional to the incident pump beam intensity (e); incident probe beam intensity (f); reflected pump beam intensity (g); reflected probe beam intensity (h); and probe modulation intensity (i), i.e. only the modulated part of the reflected probe intensity. These detector outputs are fed into a processor 66. The processor 66 calculates from the inputs the fractional change in the sample's reflectivity R (i.e. $\Delta R/R$), and normalizes this change by the intensity of the incident pump beam.

In the apparatus of this invention the detector input designated as (a) contains a modulated component which carries the information about the heat flow in addition to a large unmodulated reflected probe component 21b'. Input (b) is proportional to the unmodulated portion of the probe signal 21b. The output (i) is a voltage proportional to only the modulated part of the probe signal, which is determined by electronically removing the unmodulated component from the input (a). This output goes to a bandpass filter and preamplifier 62, then to a synchronous demodulator 64 (e.g. a lock-in amplifier), and finally to the processor 66 where it is digitized and stored. The inputs (a) and (b) are also used to determine the reflectivity of the sample corresponding to the probe beam 21b, and similarly inputs (d) and (c) are used to determine the reflectivity of the sample corresponding to the pump beam 21a. These quantities may be used to validate the optical simulation of the structure, or in some cases to deduce layer properties such as thickness in accordance with known optical reflectometry principles. In addition, inputs (a) and (d) are used by the processor 66 to normalize the reflectivity change output (i). The energy deposited in the sample 51 by the pump beam 21a may be determined by comparing the incident and reflected pump and probe beam intensities (21a', 21b').

Portions of the pump and probe beams may also be directed via beam splitter 54 onto one or more position sensitive detectors (autofocus detector 58) whose output may be used by the processor 66, in conjunction with the sample translation stage 50, to effect an optimum focus of the pump and probe beams on the sample 51. The signal to noise ratio may be improved by placing color filters and/or polarizers between the sample 51 and detector 60 to prevent light scattered from other parts of the system from impinging one or more detectors (as an example, to prevent pump light scattered from the sample 51 from impinging on reflected probe intensity detector (a)). The signal quality may be further improved by passing the modulated probe intensity output (i) from the detector 60 through the synchronous demodulator 64 (such as a lock-in amplifier, or signal averager) located before the processor 66. The signal quality may be further improved for samples 51 tending to scatter the pump beam 21a into the probe detector by introducing a second intensity modulator into the probe beam path between the source 10 and the sample 51. The second intensity modulator has a modulation frequency differing from the pump beam modulation frequency by an amount such that the difference frequency is greater than the input bandwidth of the synchronous demodulator 62. The detector output (i) corresponding to the reflected probe intensity may then be synchronously demodulated at the difference frequency, while the components; of (i) at the modulation frequencies are rejected.

Figure 3A:
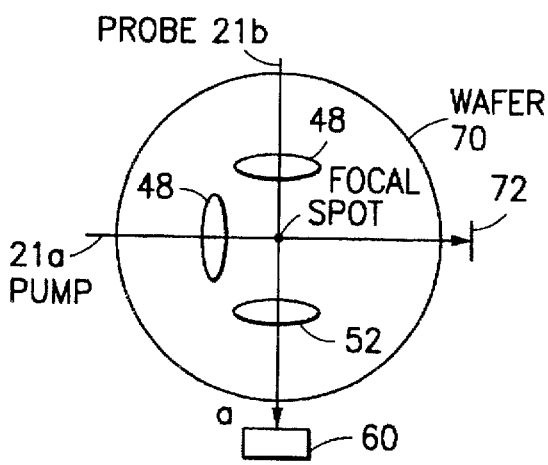
FIGS. 3a, 3b, 3c, 3d, 3e, 3f each depict an embodiment of a pump beam/probe beam delivery technique to a surface of a sample.
Figure 3B:
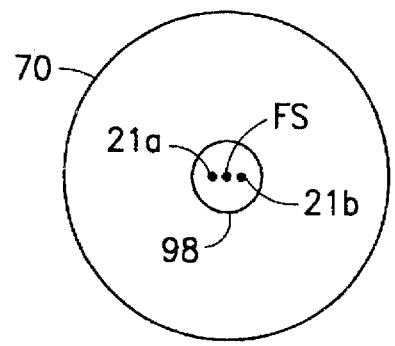
Figure 3C:
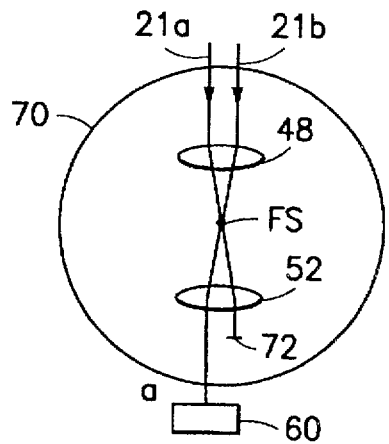
Figure 3D:
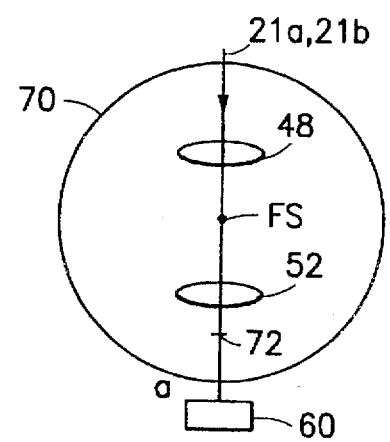
Figure 3E:
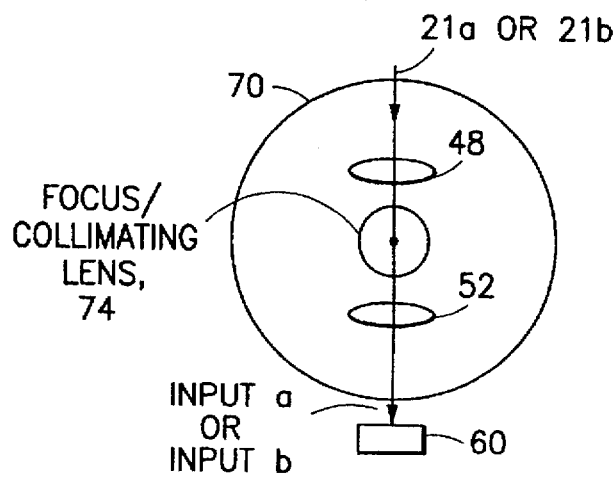
Figure 3F:
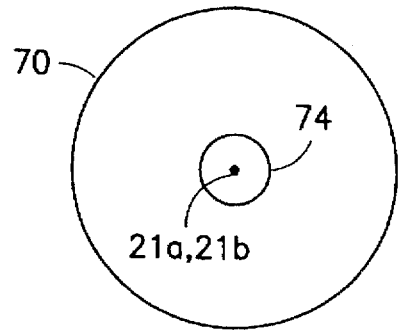

The pump and probe beams may be focused, as in FIG. 2, onto the sample through the common lens 48. This arrangement is simple to practice but is not optimal for all cases, since the pump beam 21a need be scattered through only a small angle by a non-ideal sample to impinge on the reflected probe detector (a), thereby introducing noise to the measurement of the modulated probe intensity. The common lens approach also has the weakness of achieving non-optimal spot overlap, which may be improved by using separate lenses, or coaxial beams. The common lens approach is represented in FIG. 3d in plan view from a location along a normal to the sample, here a semiconductor wafer 70. Other focusing geometries may give improved signal quality, depending on the properties of the sample (e.g. the amount of surface roughness), and the source (e.g. pump and probe beams having different colors, versus pump and probe beams having the same color).

Figure 6:
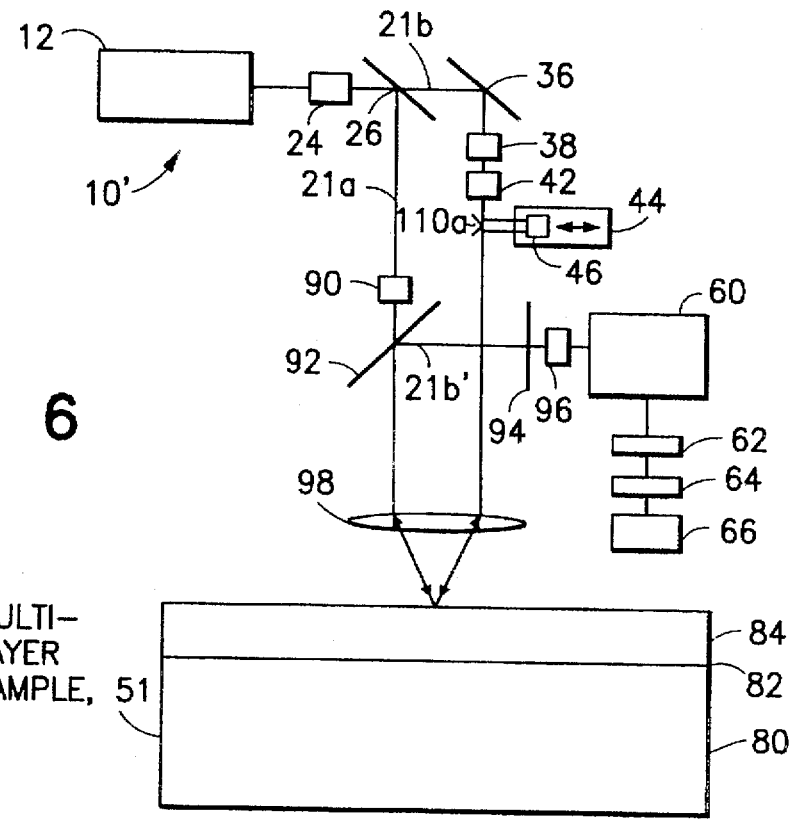
FIG. 6 illustrates a second embodiment of the interface characterization system in accordance with this invention.

Alternative focusing geometries are also illustrated in FIG. 3, and include:

(FIG. 3a) pump and probe beams oblique to the sample plane (i.e., the surface of wafer 70) and not parallel or coaxial to each other;

(FIG. 3b) pump and probe beams substantially normal to the sample plane and parallel, focused through a common lens 98 (as in FIG. 6);

(FIG. 3c) pump and probe beams parallel and lying in a plane orthogonal to the plane of incidence, focused through common lenses 48 and 52;

(FIG. 3e) (i) pump beam normal and probe beam oblique, focused independently; or (ii) probe normal and pump oblique; and (FIG. 3f) pump beam and probe beam both normal to the sample plane and coaxial, focused through a common lens 74.

Figure 9:
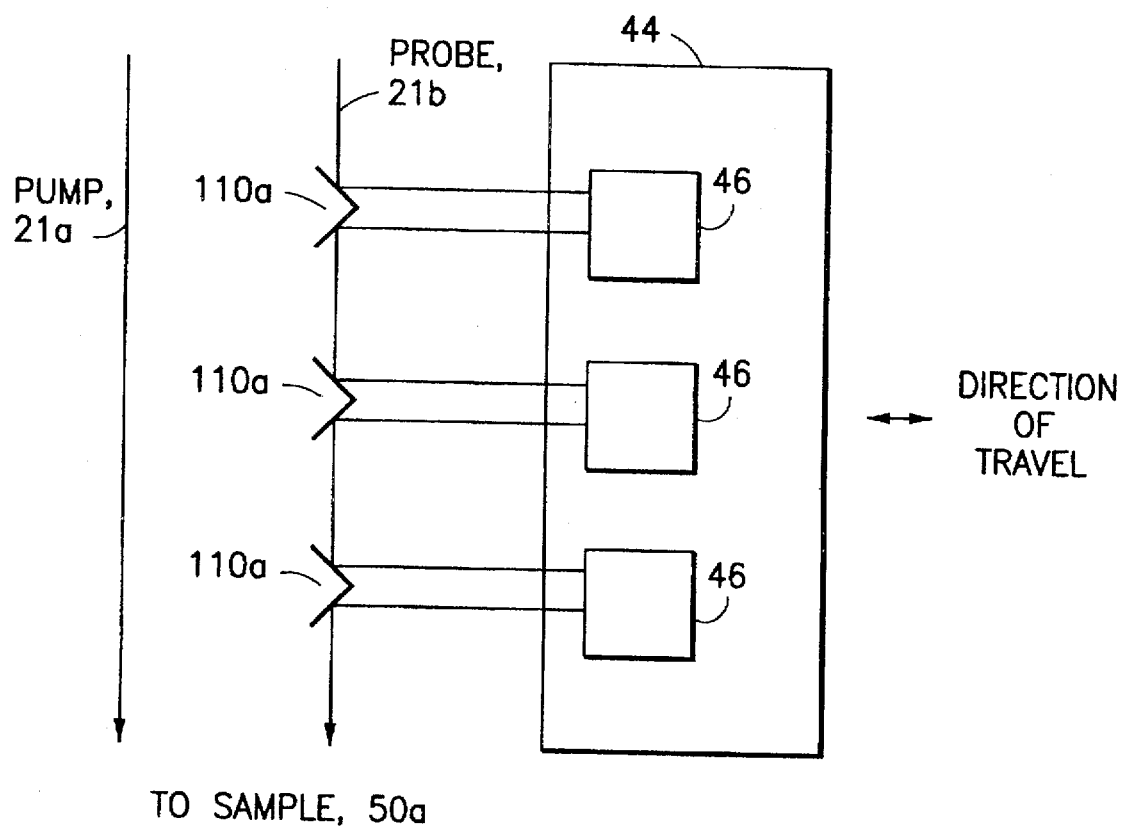
FIG. 9 illustrates an embodiment of a delay stage used for setting a delay between the pump and probe beam pulses.

The variable delay between the pump and probe beams may be implemented as shown in FIG. 2 by means of the computer controlled delay stage 44 in the probe beam path. Alternatively, a similar delay stage may be inserted within the pump beam path to "advance" the pump beam pulses in time relative to the probe pulses. An extremely long delay may be implemented as shown in FIG. 9 by placing more than one retroreflector 46 on the single translation stage 44. In this embodiment a plurality of the beam steering mirrors 110a are employed to direct the probe beam 21b to individual ones of the retroreflectors 46, thereby significantly increasing the probe beam path length relative to the pump beam path length. It is possible to implement a delay which is longer than the time between successive pulses such that the effects of a pump pulse arriving at the sample more than one pulse interval before the probe may be detected.

Figure 5:
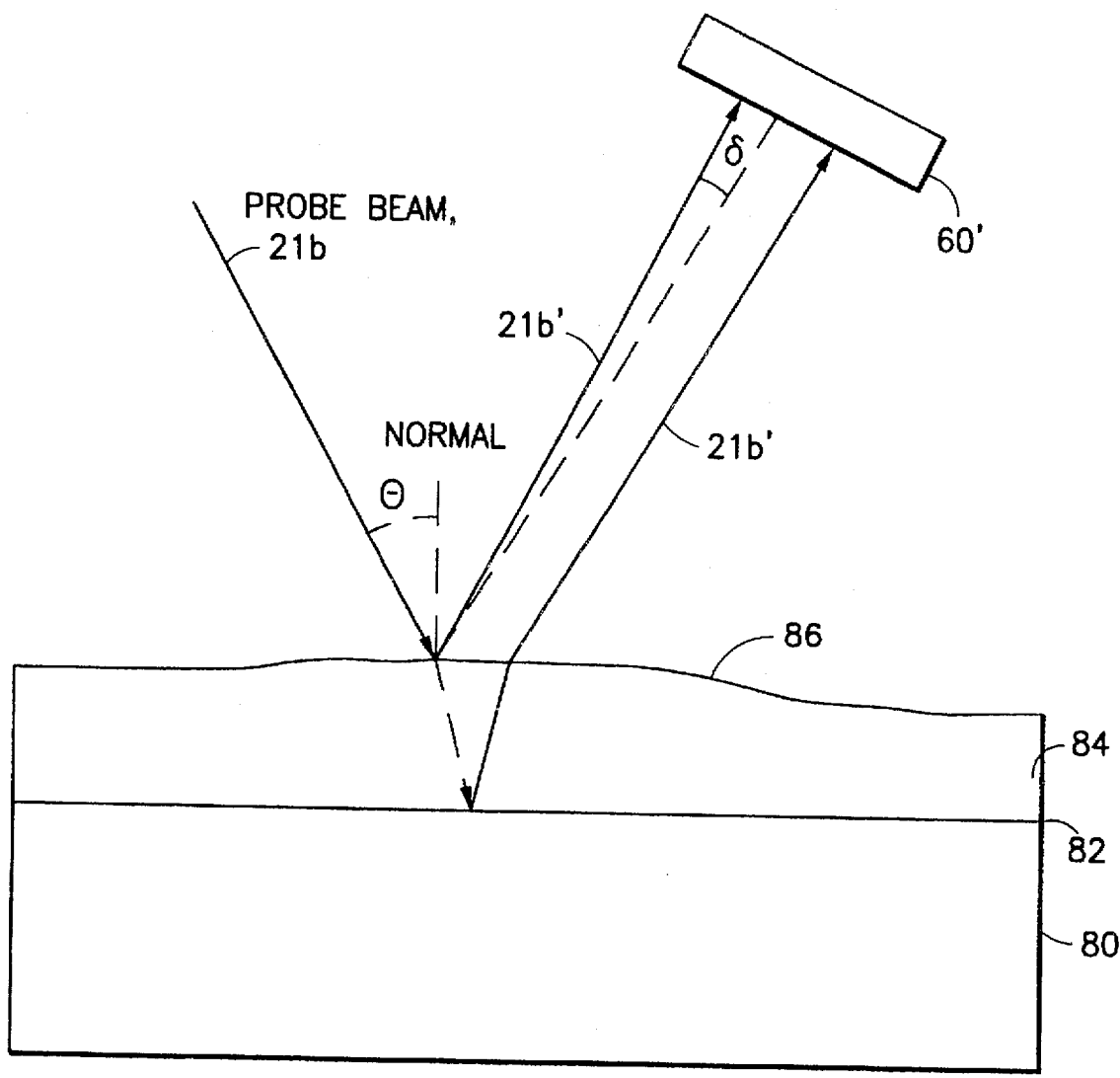
FIG. 5 is a cross-sectional, enlarged view of a sample having a substrate, a thin film layer, and an interface between the substrate and the thin film layer, and that further illustrates a thermally-induced deformation in the thin film wherein constructive and destructive probe beam interference occurs.

Referring now to FIG. 5, there is illustrated a deflection through an angle δ of the probe beam 21b' by a non-uniform expansion of a region wherein there is a temperature change (i.e. a bulge 86 in the film 84). The bulge 86 is caused at least in part by a temperature change which may also have a non-uniform profile across the spot. The deflection can be detected by a position-sensitive detector such as a split cell 60'. Deflection of the reflected probe beam 21a' can also come about in the absence of the bulge 86 due to a heat-induced change of the refractive index varying with position across the surface of the sample. This deflection can also be detected by a position sensitive detector. FIG. 5 also illustrates the lengthening of the path through the sample as a result of the surface displacement (uniform or non-uniform).

FIG. 6 illustrates a configuration which is based on FIGS. 1, 2 and 3, and is a preferred implementation of a "normal incidence, dual wavelength" system. The source 10' (FIG. 1b) is frequency doubled using the nonlinear crystal 24, such as BBO, KTP or LBO. The pump and probe beams are separated by the dichroic mirror 26 such that the doubled wavelength is passed to become the probe beam 21b, and the undoubted part is reflected to become the pump beam 21a. The pump beam 21a is modulated by modulator 90 and is directed at normal incidence onto the sample 51 through objective 98. The probe beam polarization is rotated by means of a half wave plate 38 and is then passed through a polarizer 42 oriented to be orthogonal to the pump beam polarization. This retarder/polarizer combination is also used as a variable attenuator for the probe beam 21b. The probe beam 21b is then sent to the variable delay stage 44, and is focused onto the sample 51 through the same normal incidence objective 98 as the probe beam 21a. The reflected probe beam 21b' is directed to the detector 60 by a dichroic mirror 92 which passes the reflected pump beam 21a, thereby effectively filtering out any reflected probe light. A filter 94 which passes only the probe beam wavelength is placed before the detector 60. The detector 60 is followed by the tuned filter 62, lock-in amplifier 64, and processor 66, as in FIG. 2.

Figure 7:
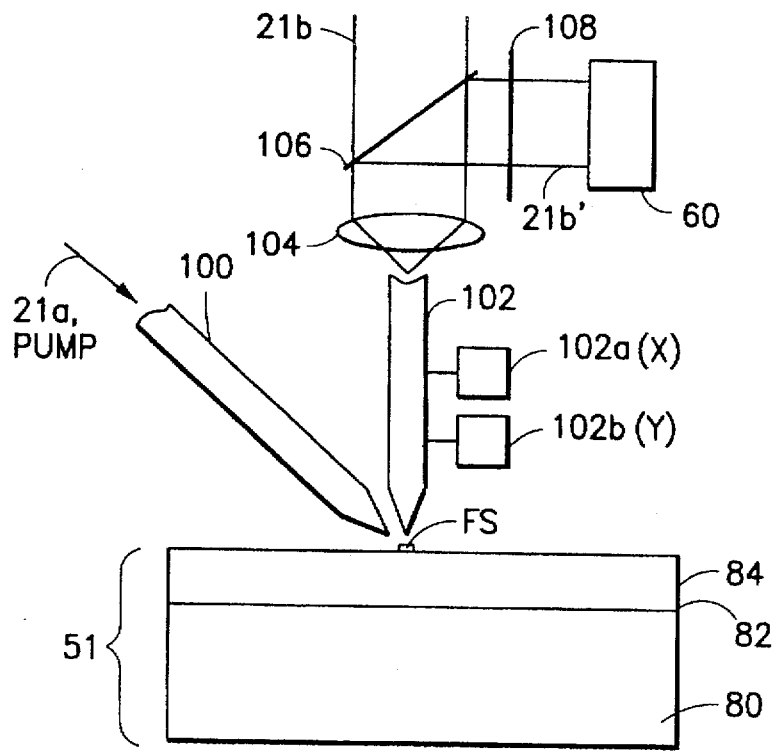
FIG. 7 illustrates a fiber optic-based pump and probe beam delivery and focussing system in accordance with an embodiment of this invention.

FIG. 7 illustrates an embodiment of this invention wherein the pump beam 21a and the probe beam 21b are directed to the sample 51 by means of tapered optical fibers 100 and 102, respectively, to achieve near-field focusing and FS sizes of order 100 nm. The probe beam 21b is shown having normal incidence, and may have a different wavelength than the pump beam 21a. In this embodiment a terminal portion of the pump and/or probe beam delivery fiber 100, 102 is reduced in diameter, such as by stretching the fiber, so as to provide a focussed spot FS having a diameter that is less than the normal range of optical focussing. This enables the pump and/or probe optical pulse to be repeatably delivered to a very small region of the sample's surface (e.g., to a spot having a diameter<one micrometer), regardless of any changes that are occurring in the optical path length of the pump and/or probe beam.

The pump beam 21a need not be brought in through a fiber, and in one mode of operation may be much larger than the probe spot size on the sample. The probe beam 21b may then be scanned by x-axis and y-axis piezoelectric actuators 102a and 102b on a very small spatial scale (similar to a Scanning Tunneling Microscope) with the pump beam location fixed. This embodiment may be used to map structures patterned in two or more dimensions on a length scale smaller than can be achieved using conventional lithography. Therefore, it can be used to map the smallest structure s found in integrated circuits.

The probe beam 21b can be an expanded beam that is focused onto the fiber 102 by a lens 104, and the reflected probe beam 21b' is directed through the fiber 102 and is diverted by a splitter 106 to a filter 108 and then to the detector 60.

Figure 12:
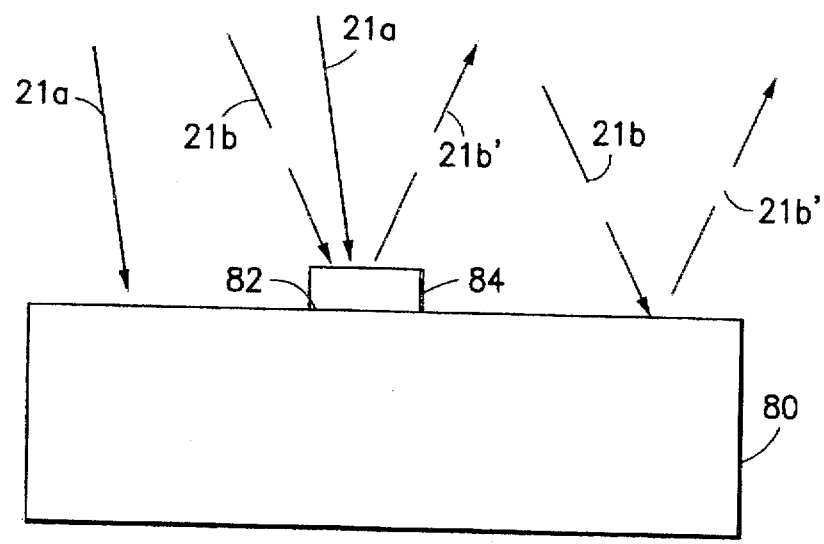
FIG. 12 is a cross-sectional, enlarged view of the sample having the substrate, a localized thin film structure disposed on a surface of the substrate, and the interface between the substrate and the thin film structure, and that further illustrates various methods to apply the pump and probe beams.

FIG. 12 illustrates an interface 82 between a patterned structure 84 on top of the substrate 80, and is useful in explaining the use of this invention when characterizing three dimensional structures (e.g., nanostructures). The interface 82 may be evaluated by depositing heat in the substrate 80, and detecting it in the structure 84; or by depositing heat in the structure 84 and detecting it in the structure 84, or in the substrate 80.

Figure 13:
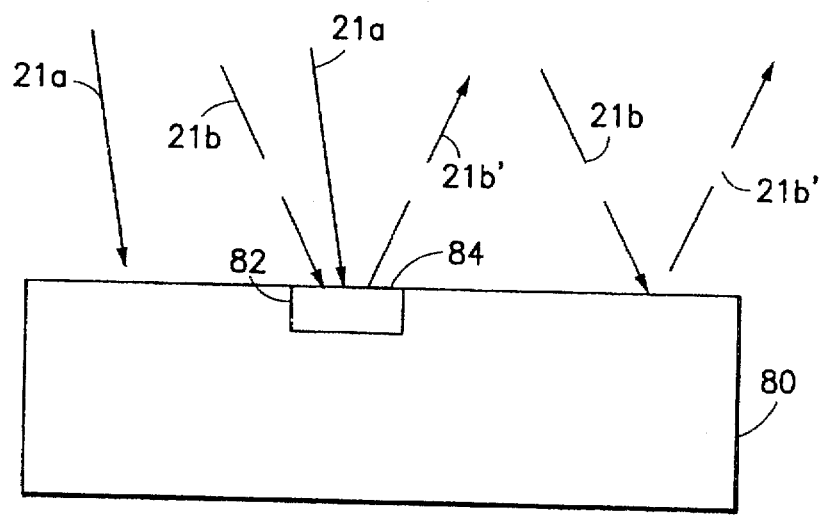
FIG. 13 is a cross-sectional, enlarged view of the sample having the substrate, a localized thin film structure disposed within a surface of the substrate, and the interface between the substrate and the thin film structure, and that further illustrates various methods to apply the pump and probe beams.

FIG. 13 shows an interface 82 surrounding a structure 84 is formed within a patterned recess within a surface of substrate 80. An example of this three dimensional configuration is a tungsten via formed in a hole in a glass layer by (i) depositing the glass on a substrate, (ii) patterning and etching the hole, (iii) depositing a film of tungsten and (iv) polishing the tungsten layer until the glass is exposed (adhesion promoting layers may be deposited before the tungsten). The interface 82 may be evaluated by depositing heat in the substrate 80 (not applicable if the substrate, as in the above tungsten example, is glass) and detecting it in the embedded structure 84; or by depositing heat in the structure 84 and detecting it in the structure 84, or in the substrate 80 (which can apply to the above tungsten example).

It should be realized that, in the three dimensional structures illustrated in FIGS. 12 and 13, the pump beam can also be employed to excite the normal modes in the structure, which can in turn affect the transmitted or reflected probe beam.

It should be further realized that the value of $R_K$ can also depend in some degree to the stress in the film or substrate. As such, after determining the value of $R_K$ a correlation may be made with the amount of stress in the structure, for example, an amount of residual stress remaining after annealing the structure. The correlation can be accomplished using a value of $R_K$ obtained from a reference structure, and/or from simulations of the stress in the structure.

Figure 14:
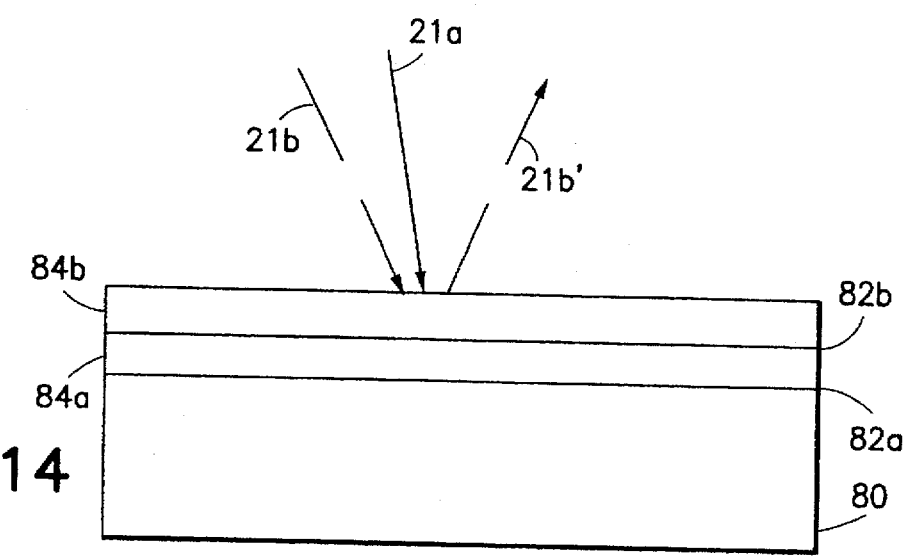
FIG. 14 is a cross-sectional, enlarged view of a sample having a substrate, a plurality of thin film layers, and interfaces between the substrate and one of the thin film layers and between the thin film layers.

FIG. 14 shows that for samples considered in the heat flow technique a multilayer thin film 84a, 84b may be substituted for a simple film 84. Such multilayer films may be formed intentionally by sequential depositions, or unintentionally because the substrate 80 may have been ineffectively cleaned prior to succeeding layer depositions, or by a (intentional or unintentional) chemical reaction between two or more layers (for example, following heat treatment). Such layers may cause a change in the cooling rate of films above them, or may give rise to ultrasonic echoes having complicated shapes and temporal characteristics. It is possible to determine the thicknesses and interface characteristics for thin film structures containing, by example, five or more sublayers. This is preferably accomplished by comparing the reflectivity data with simulations of the heat flow and detection physics to obtain a best fit set of unknowns with the obtained data.

When applying the probe beam 21b to the structure 84 it may be advantageous to use a near-field focussing arrangement, such as the tapered optical fiber shown in FIG. 7. In this case the pump beam FS can be significantly larger than the probe beam FS, thereby enabling the selective probing of small scale structures.

This capability for spatial imaging can be exploited to perform measurements of Kapitza resistance with lateral spatial resolution to 100 nm scale and below.

It is also within the scope of this invention to apply a pump beam FS and a probe beam FS to simultaneously probe a plurality of patterned structures (e.g., a two-dimensional array of tungsten vias 0.5 μm in diameter and 1.0 μm apart that are formed in a substrate). In this case each tungsten via may be considered a separate, independent element, each of which contributes to the reflected or transmitted probe beam signal. For closer spacings between elements, the rate of cooling of one element is affected by the heat released from adjacent elements excited, i.e., there are coupling effects between the vias. In either case the probe beam signal can be compared to a signal obtained from a reference "known good" structure, or to a simulation of the structure, or from a combination of reference data and simulations. Any deviation in the probe signal from the reference and/or simulated signal may indicate that the sample differs in some way from what was expected.

In the system configurations which use the AOM 40 to modulate the pump beam 21a, there may be no relationship between the modulation rate and the repetition rate of the laser 12. As a result, the laser pulse train and modulation cycle are asynchronous. It is possible to make this a synchronous system by deriving the modulation rate from the pulse repetition rate. The pulse repetition rate may be obtained from the laser 12 by means of an optical detector which senses the emitted pulses, or by using the drive signal from an actively mode-locked laser. To derive the modulation signal, the pulse rate signal is applied to a counter which changes the state of the modulator 40 after n laser pulses are counted. The modulation rate is then ½ n times the laser pulse rate. In such a synchronous scheme the number of pump pulses impinging on the sample 51 in any period of the modulator 40 is always the same. This eliminates a potential source of noise in the modulated probe beam 21b which might arise in an asynchronous system under conditions in which the laser energy contained within a single cycle of the modulator 40 varies from period to period of the modulation.

A major source of noise is scattered pump light which can reach the probe beam detector (a) despite having a nominally orthogonal polarization (polarizers are not perfect, and also the sample 51 may tend to depolarize the light). As was described above, one technique to suppress this source of noise is to use pump and probe beams of different color, so that the pump color may be blocked by means of a filter before the probe detector.

Another method is to modulate the probe beam 21b at a frequency different from the pump beam modulation frequency. By example, if the pump modulation frequency is $f_1$ and the probe modulation frequency is $f_2$, then the part of the probe beam modulated by the pump beam at the sample 51 will have a component at the frequency $f_1-f_2$. This signal may be passed through a synchronous demodulator or low pass filter designed to reject $f_1$ and $f_2$ and pass only their difference frequency. Thus, any pump light scattered by the sample 51 onto the probe detector (a), which would otherwise appear as noise in the data, is suppressed. To minimize the introduction of ubiquitous 1/f noise the difference frequency is preferably not below a few hundred kHz. Exemplary frequencies are $f_1=1$ MHz and $f_2=500$ kHz.

Measurements at two angles can be simultaneously made by detecting parts of the probe beam 21b impinging on the sample 51 within a single focused beam, which then reflects to two or more closely spaced detectors. One can also controllably tilt the sample stage 50, and to thus cause the probe beam 21b to impinge on the surface of the sample 51 at two or more different angles of incidence.

Figure 15:
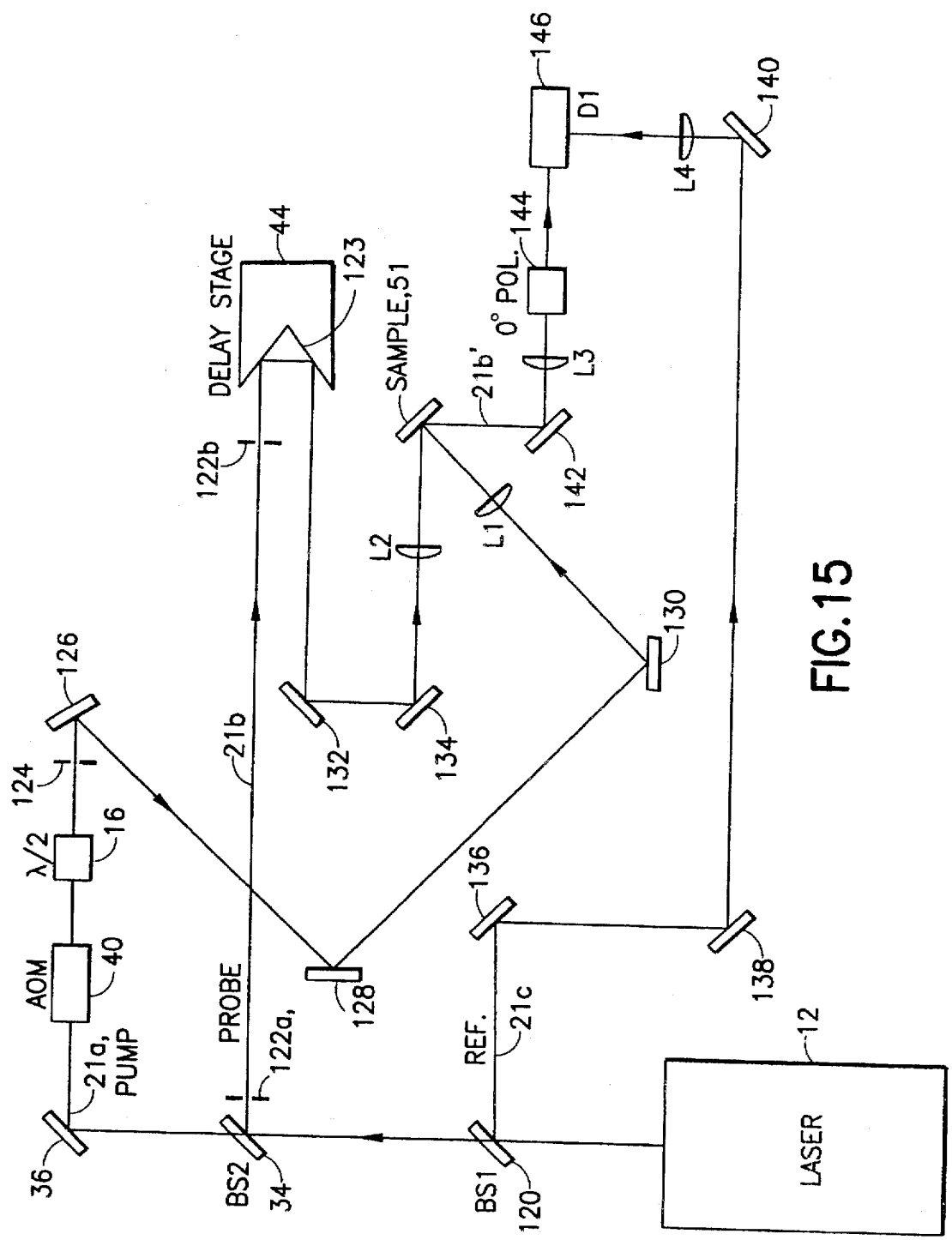
FIG. 15 illustrates in greater detail one suitable embodiment of the measuring system.

A block diagram of one suitable embodiment of the system is shown in FIG. 15. The light pulses are produced by a dye laser 12 operating at 6320 Å (Coherent Satori 774) pumped with 2 W of 532 nm light from a frequency-doubled mode-locked YAG laser (Coherent Antares 76-S Nd YAG). The pulse duration is 0.2 ps FWHM, the repetition rate is 76 MHz, and the energy of each light pulse from the laser 12 is 2 nJ. The output of the laser 12 is divided into pump-and-probe beams by means of a beam splitter BS2. The pump beam is chopped at 1 MHz by the AOM 40 and the polarization is rotated 90° by the half-wave plate 16. The pump beam path can include a number of optical components, such as an aperture 124 and relay mirrors 126, 128 and 130. The pump pulse is focused to a spot on the sample 51 of diameter 5 to 20 µm by lens L1, and the energy in each pump pulse applied to the sample 51 is typically 0.5 nJ. The optical path length for the pump beam 21a remains constant during the measurement. The probe beam 21b passes through apertures 122a and 122b, is reflected at a corner-cube mirror 123 mounted on the mechanical translation stage 44, is relayed by mirrors 132 and 134, and is then focused by lens L2 onto the same region of the sample 51 that is illuminated by the pump beam 21a. Displacement of the mechanical stage 44 is used to vary the time delay of the probe beam 21b relative to the pump beam 21a. In this embodiment a delay stage motion of 75 cm (150 cm round trip) gives a delay of 5 nsecs. The reflected probe light 216' is collected by lens L3 and passed through a polarizer 0° POL 144. The polarizer 144 is used to remove any scattered pump light from the reflected probe beam 21a' before the reflected probe beam is detected by a photodiode detector D1 (146). The detector D1 uses a reference beam from a reference beam splitter BS1 120 to reduce the effective laser noise. To improve the signal to noise ratio the output of the photodiode D1 is amplified by a lock-in amplifier (not shown) which has as its reference source the same 1 MHz signal that is used to drive the AOM 40. The measurement procedure thus records the lock-in output while the position of the mechanical stage 44 is swept to give the required range of time delays of the probe beam 21b. In practice, this motion of the stage 44 is repeated a number of times and the results averaged to further improve the signal-to-noise ratio.

It is possible to use techniques in which a mechanical stage is completely avoided. One way to do this is to use a continuous laser for the probe beam and a fast photodiode detector to sense the changes in sample reflectivity induced by the pump. This approach can be used for measurements of $\Delta R(t)$ for times t comparable to, or greater than, the response time of the photodiode and associated electronics, i.e. of the order of 100 picoseconds. However, this approach is not preferred for a measurement of $\Delta R(t)$ over the entire range from below 1 psec out to nsecs.

A second, related approach is to use two lasers running at slightly different repetition rates, as in FIG. 1c, one for the pump and the other for the probe. The time delay between pump and probe beam pulses increases at a rate determined by the difference in laser repetition rates and, thus, no mechanical stage is required. This method has the disadvantage that it requires two pulsed lasers systems.

It is important to note that there may be a displacement of one surface relative to another due to thermal expansion (e.g., see FIG. 5), stress waves, vibrations, etc. Interference between parts of the probe beam 21b reflected by two or more surfaces causes a change in the intensity of the detected probe beam 21b' along direction θ. This intensity change is comparable to the change observed from the change in the optical constants described by Tauc et al. Displacement effects such as this play a role whenever one or more layers is semi-transparent.

In the system configurations which use the AOM 40 to modulate the pump beam 21a, there may be no relationship between the modulation rate and the repetition rate of the laser 12. As a result, the laser pulse train and modulation cycle are asynchronous. It is possible to make this a synchronous system by deriving the modulation rate from the pulse repetition rate. The pulse repetition rate is obtained from the laser 12 by means of an optical detector which senses the emitted pulses, or by using the drive signal from an actively mode-locked laser. To derive the modulation signal, the pulse rate signal is applied to a counter which changes the state of the modulator 40 after n laser pulses are counted. The modulation rate is then ½ n times the laser pulse rate. In such a synchronous scheme the number of pump pulses impinging on the sample 51 in any period of the modulator 40 is always the same. This eliminates a potential source of noise in the modulated probe beam 21b which might arise in an asynchronous system under conditions in which the laser energy contained within a single cycle of the modulator 40 varies from period to period of the modulation.

A major source of noise is scattered pump light which can reach the probe beam detector (a) despite having a nominally orthogonal polarization (polarizers are not perfect, and also the sample 51 may tend to depolarize the light). As was described above, one technique to suppress this source of noise is to use pump and probe beams of different color, so that the pump color may be blocked by means of a filter before the probe detector. Another method, also described previously, is to modulate the probe beam 21b at a frequency close to, but different from, the pump beam modulation frequency. By example, if the pump modulation frequency is $f_1$ and the probe modulation frequency is $f_2$, then the part of the probe beam modulated by the pump beam at the sample 51 will have a component at the frequency $f_1-f_2$. This signal may be passed through a synchronous demodulator or low pass filter designed to reject $f_1$ and $f_2$ and pass only their difference frequency. Thus, any pump light scattered by the sample 51 onto the probe detector (a), which would otherwise appear as a source of noise in the data, does not enter the data. To minimize the introduction of ubiquitous 1/f noise the difference frequency is preferably not below a few hundred kHz. Exemplary frequencies are $f_1$=1 MHz and $f_2$=500 kHz.

Figure 16:
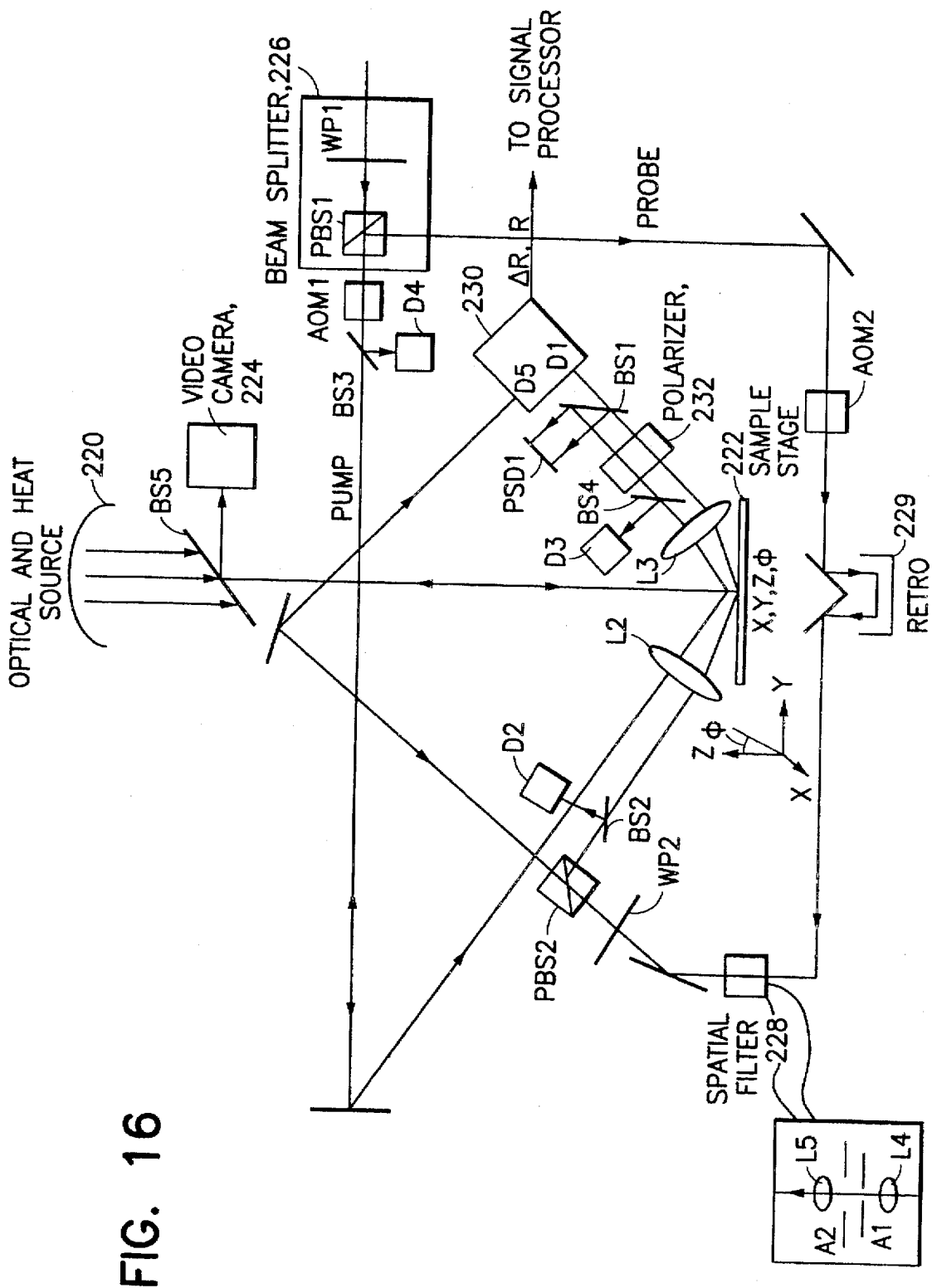
FIG. 16 is a block diagram of a first embodiment of a picosecond measurement system that is suitable for practicing this invention, specifically, a parallel, oblique beam embodiment.

Reference is now made to FIG. 16 for illustrating an embodiment of a measurement system which is referred to as a parallel, oblique embodiment.

This embodiment includes an optical/heat source 220, which functions as a variable high density illuminator, and which provides illumination for a video camera 224 and a sample heat source for temperature-dependent measurements under computer control. An alternative heating method employs a resistive heater embedded in the stage sample stage 222.

The advantage of the optical heater is that it makes possible rapid sequential measurements at two different temperatures, as will be described below. The video camera 224 provides a displayed image for an operator, and facilitates the set-up of the measurement system. Appropriate pattern recognition software can also be used for this purpose, thereby minimizing or eliminating operator involvement.

The sample stage 222 is preferably a multiple-degree of freedom stage that is adjustable in height (z-axis), position (x and y-axes), and tilt (θ), and allows motor controlled positioning of a portion of the sample relative to the pump and probe beams. The z-axis is used to translate the sample vertically into the focus region of the pump and probe, the x and y-axes translate the sample parallel to the focal plane, and the tilt axes adjust the orientation of the stage 222 to establish a desired angle of incidence for the probe beam. This is achieved via detectors PDS1 and PDS2 and the local processor, as described below.

In an alternative embodiment, the optical head may be moved relative to a stationary, tiltable stage 222' (not shown). This is particularly important for scanning large objects (such as 300 mm diameter wafers, or mechanical structures, etc.) In this embodiment the pump beam, probe beam, and video are delivered to the translatable head via optical fibers or fiber bundles.

BS5 is a broad band beam splitter that directs video and a small amount of laser light to the video camera 224. The camera 224 and local processor can be used to automatically position the pump and probe beams on a measurement site.

The pump-probe beam splitter 226 splits an incident laser beam pulse (preferably of picosecond or shorter duration) into pump and probe beams, and includes a rotatable half-wave plate (WP1) that rotates the polarization of the unsplit beam. WP1 is used in combination with polarizing beam splitter PBS1 to effect a continuously variable split between pump and probe power. This split may be controlled by the computer by means of a motor to achieve an optimal signal to noise ratio for a particular sample. The appropriate split depend on factors such as the reflectivity and roughness of the sample. Adjustment is effected by having a motorized mount rotate WP1 under computer control.

A first acousto-optic modulator (AOM1) chops the pump beam at a frequency of about 1 MHz. A second acousto-optic modulator (AOM2) chops the probe beam at a frequency that differs by a small amount from that of the pump modulator AOM1. The use of AOM2 is optional in the system illustrated in FIG. 16. As will be discussed below, the AOMs may be synchronized to a common clock source, and may further be synchronized to the pulse repetition rate (PRR) of the laser that generates the pump and probe beams.

A spatial filter 228 is used to preserve at its output a substantially invariant probe beam profile, diameter, and propagation direction for an input probe beam which may vary due to the action of the mechanical delay Line shown as the retroreflector 229. The spatial filter 283 includes a pair of apertures A1 and A2, and a pair of lenses L4 and L5.

WP2 is a second adjustable half wave plate which functions in a similar manner, with PBS2, to the WP1/PBS1 of the beamsplitter 226. With WP2 the intent is to vary the ratio of the part of the probe beam impinging on the sample to that of the portion of the beam used as a reference (input to D5 of the detector 230. WP2 may be motor controlled in order to achieve a ratio of approximately unity. The electrical signals produced by the beams are subtracted, leaving only the modulated part of the probe to be amplified and processed. PSD2 is used in conjunction with WP2 to achieve any desired ratio of the intensities of the probe beam and reference beam. The processor may adjust this ratio by making a rotation of WP2 prior to a measurement in order to achieve a nulling of the unmodulated part of the probe and reference beam. This allows the difference signal (the modulated part of the probe) alone to be amplified and passed to the electronics.

The beamsplitter BS2 is used to sample the intensity of the incident probe beam in combination with detector D2.

The linear polarizer 232 is employed to block scattered pump light polarization, and to pass the probe beam. Lenses L2 and L3 are pump and probe beam focusing and collimating objectives respectively. The beamsplitter BS1 is used to direct a small part of pump and probe beams onto a first Position Sensitive Detector (PSD1) that is used for autofocusing, in conjunction with the processor and movements of the sample stage 222. The PSD1 is employed in combination with the processor and the computer-controlled stage 222 (tilt and z-axis) to automatically focus the pump and probe beams onto the sample to achieve a desired focusing condition.

The detector D1 may be used in common for heat flow, ellipsometry and reflectometry embodiments of this invention. However, the resultant signal processing is different for each application. For heat flow, the DC component of the signal is suppressed such as by subtracting reference beam input D5, or part of it as needed, to cancel the unmodulated part of D1, or by electrically filtering the output of D1 so as to suppress frequencies other than that of the modulation. The small modulated part of the signal is then amplified and stored. For ellipsometry, there is no small modulated part, rather the entire signal is sampled many times during each rotation of the rotation compensator (see FIG. 17), and the resulting waveform is analyzed to yield the ellipsometric parameters. For reflectometry, the change in the intensity of the entire unmodulated probe beam due to the sample is determined by using the D1 and D2 output signals (D2 measures a signal proportional to the intensity of the incident probe). Similarly, additional reflectometry data can be obtained from the pump beam using detectors D3 and D4. The analysis of the reflectometry data from either or both beams may be used to characterize the sample. The use of two beams is useful for improving resolution, and for resolving any ambiguities in the solution of the relevant equations.

A third beamsplitter BS3 is used to direct a small fraction of the pump beam onto detector D4, which measures a signal proportional to the incident pump intensity. A fourth beamsplitter BS4 is positioned so as to direct: a small fraction of the pump beam onto detector D3, which measures a signal proportional to the reflected pump intensity.

Figure 17:
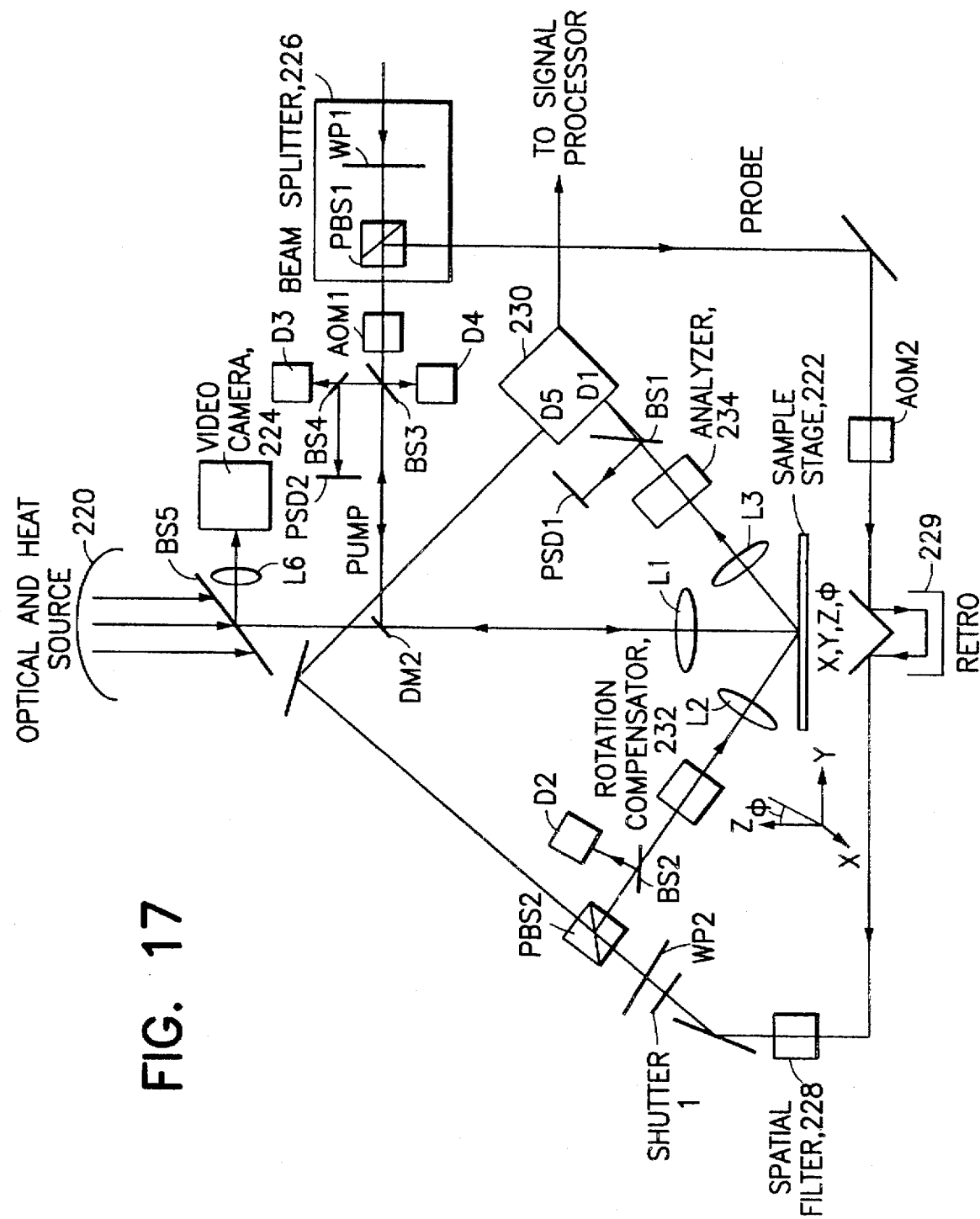
FIG. 17 is a block diagram of a second embodiment of a picosecond measurement system that is suitable for practicing this invention, specifically, a normal pump, oblique probe embodiment.

FIG. 17 illustrates a normal pump beam, oblique probe beam embodiment of this invention. Components labelled as in FIG. 16 function in a similar manner, unless indicated differently below. In FIG. 17 there is provided the above-mentioned rotation compensator 232, embodied as a linear quarter wave plate on a motorized rotational mount, and which forms a portion of an ellipsometer model of the system. The plate is rotated in the probe beam at a rate of, by example, a few tens of Hz to continuously vary the optical phase of the probe beam incident on the sample. The reflected light passes through an analyzer 234 and the intensity is measured and transferred to the processor many times during each rotation. The signals are analyzed according to known types of ellipsometry methods to determine the characteristics of the sample (transparent or semitransparent films). This allows the (pulsed) probe beam to be used to carry out ellipsometry measurements.

In accordance with an aspect of this invention the ellipsometry measurements are carried out using a pulsed laser, which is disadvantageous under normal conditions, since the bandwidth of the pulsed laser is much greater than that of a CW laser of a type normally employed for ellipsometry measurements.

When heat flow measurements are being made, the rotation compensator 232 is oriented such that the probe beam is linearly polarized orthogonal to the pump beam.

The analyzer 234 may be embodied as a fixed polarizer, and also forms a portion of the ellipsometer mode of the system. When the system is used for heat flow measurements the polarizer 234 is oriented to block the pump polarization. When used in the ellipsometer mode, the polarizer 234 is oriented so as to block light polarized at 45 degrees relative to the plane of the incident and reflected probe beam.

Finally, the embodiment of FIG. 17 further includes a dichroic mirror (DM2), which is highly reflective for light in a narrow band near the pump wavelength, and is substantially transparent for other wavelengths.

It should be noted in FIG. 17 that BS4 is moved to sample the pump beam in conjunction with BS3, and to reflect a portion of the pump to D3 and to a second PSD (PSD2). PSD2 (pump PSD) is employed in combination with the processor, computer controlled stage 222 (tilt and z-axis), and PSD1 (Probe PSD) to automatically focus the pump and probe beams onto the sample to achieve a desired focusing condition. Also, a lens L1 is employed as a pump, video, and optical heating focussing objective, while an optional lens L6 is used to focus the sampled light from BS5 onto the video camera 224.

Figure 18:
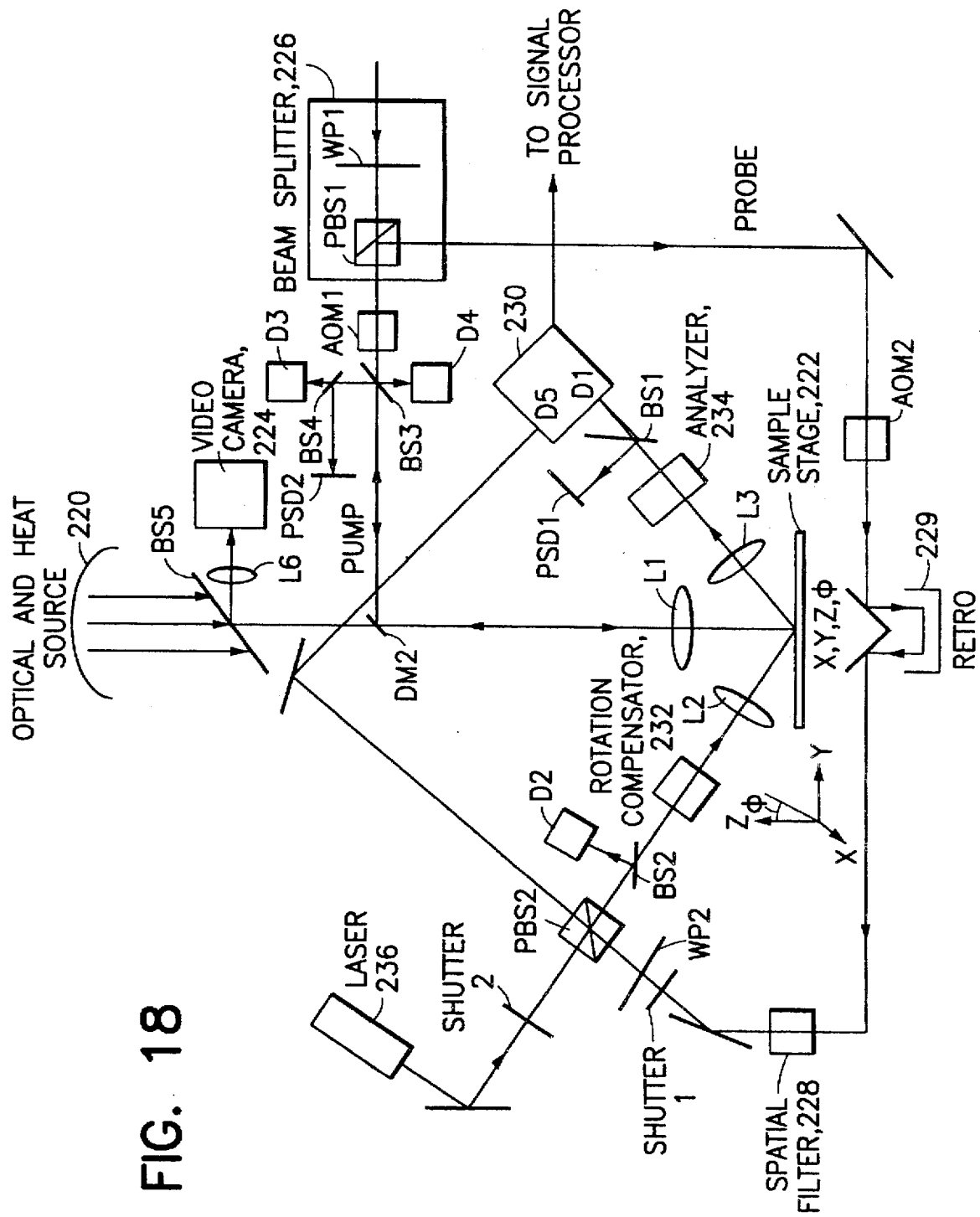
FIG. 18 is a block diagram of a third, presently preferred embodiment of a picosecond measurement system that is suitable for practicing this invention, specifically, a single wavelength, normal pump, oblique probe, combined ellipsometer embodiment.

Reference is now made to FIG. 18 for illustrating a further, presently preferred, embodiment of the picosecond measurement system, specifically a single wavelength, normal pump, oblique probe, combined ellipsometer embodiment. As before, only those elements not described previously will be described below.

Shutter 1 and shutter 2 are computer controlled shutters, and allow the system to use a He—Ne laser 236 in the ellipsometer mode, instead of the pulsed probe beam. For acoustics or heat flow measurements shutter 1 is open and shutter 2 is closed. For ellipsometer measurements shutter 1 is closed and shutter 2 is opened. The HeNe laser 236 is a low power CW laser, and has been found to yield superior ellipsometer performance for some films.

Figure 19:
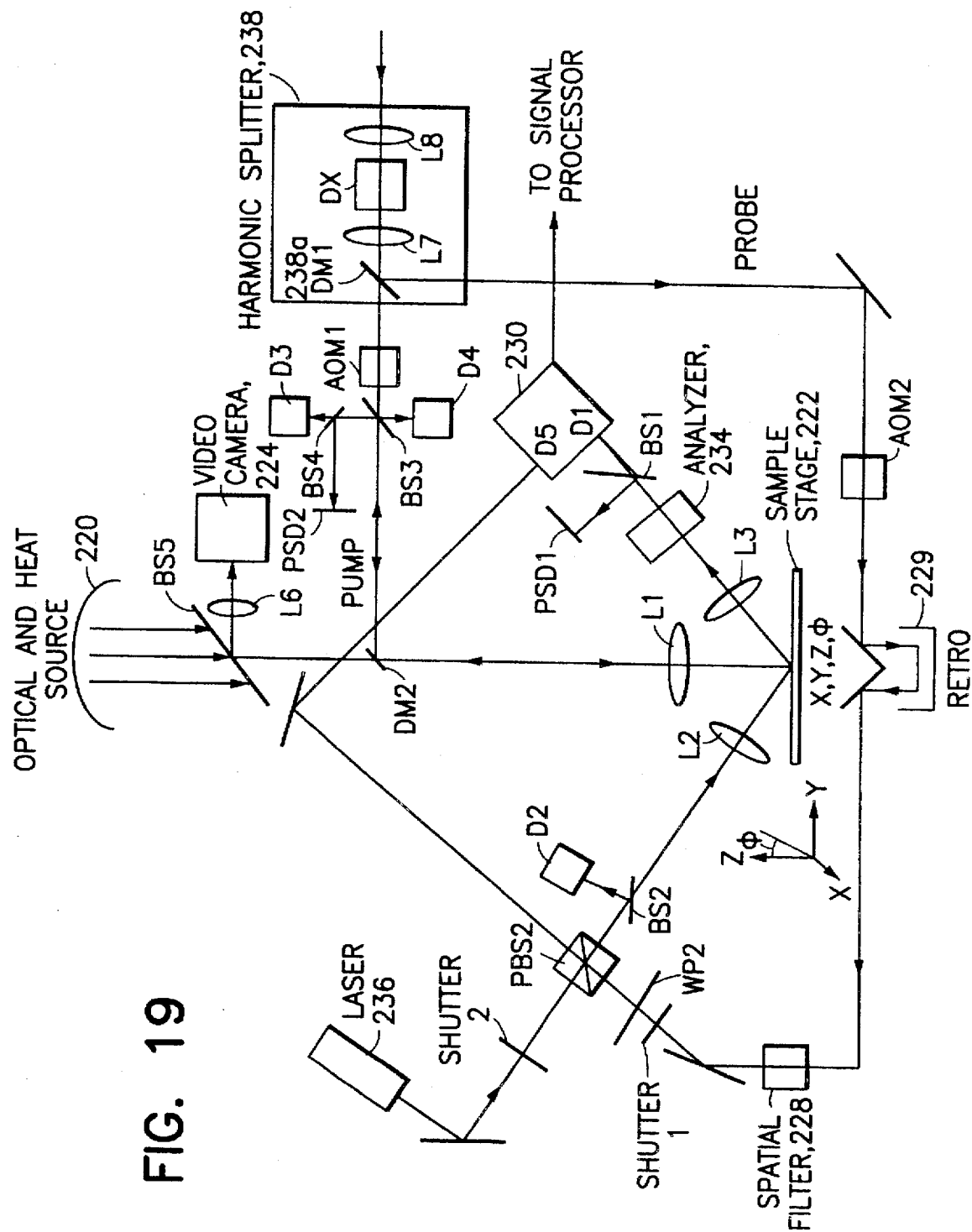
FIG. 19 is a block diagram of a fourth embodiment of a picosecond measurement system that is suitable for practicing this invention, specifically, a dual wavelength, normal pump, oblique probe, combined ellipsometer embodiment.

FIG. 19 is a dual wavelength embodiment of the system illustrated in FIG. 18. In this embodiment the beamsplitter 226 is replaced by a harmonic splitter, an optical harmonic generator that generates one or more optical harmonics of the incident unsplit incident laser beam. This is accomplished by means of lenses L7, L8 and a nonlinear optical material (DX) that is suitable for generating the second harmonic from the incident laser beam. The pump beam is shown transmitted by the dichroic mirror (DM 238a) to the AOM1, while the probe beam is reflected to the retroreflector. The reverse situation is also possible. The shorter wavelength may be transmitted, and the longer wavelength may be reflected, or vice versa. In the simplest case the pump beam is the second harmonic of the probe beam (i.e., the pump beam has one half the wavelength of the probe beam).

It should be noted that in this embodiment the AOM2 is eliminated since rejection of the pump beam is effected by means of color filter F1, which is simpler and more cost effective than heterodyning. F1 is a filter having high transmission for the probe beam and the He—Ne wavelengths, but very low transmission for the pump wavelength.

Figure 20:
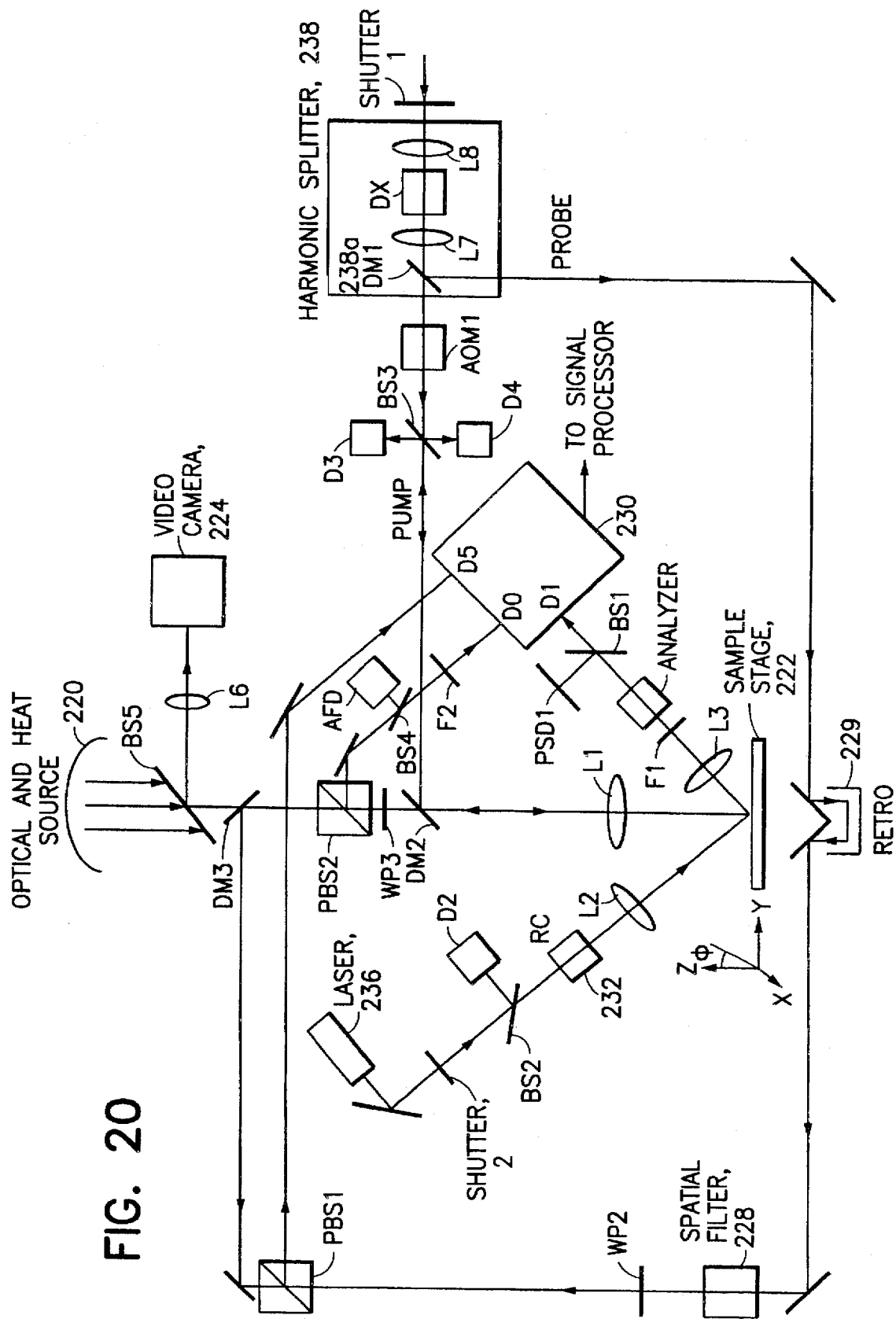
FIG. 20 is a block diagram of a fifth embodiment of a picosecond measurement system that is suitable for practicing this invention, specifically, a dual wavelength, normal incidence pump and probe, combined ellipsometer embodiment.

Finally, FIG. 20 illustrates a normal incidence, dual wavelength, combined ellipsometer embodiment of this invention. In FIG. 20 the probe beam impinges on PBS2 and is polarized along the direction which is passed by the PBS2. After the probe beam passes through WP3, a quarter wave plate, and reflects from the sample, it returns to PBS2 polarized along the direction which is highly reflected, and is then directed to a detector D0 in detector block 230. D0 measures the reflected jprobe beam intensity.

In greater detail, WP3 causes the incoming plane polarized probe beam to become circularly polarized. The handedness of the polarization is reversed on reflection from the sample, and on emerging from WP3 after reflection, the probe beam is linearly polarized orthogonal to its original polarization. BS4 reflects a small fraction of the reflected probe onto an Autofocus Detector AFD.

DM3, a dichroic mirror, combines the probe beam onto a common axis with the illuminator and the pump beam. DM3 is highly reflective for the probe wavelength, and is substantially transparent at most other wavelengths. D1, a reflected He—Ne laser 236 detector, is used only for ellipsometric measurements.

It should be noted that, when contrasting FIG. 20 to FIGS. 18 and 19, that the shutter 1 is relocated so as to intercept the incident laser beam prior to the harmonic splitter 238.

Based on the foregoing descriptions of a number of embodiments of this invention, it can be appreciated that this invention teaches, in one aspect, a picosecond optical system for the characterization of samples in which a short optical pulse (the pump beam) is directed to an area of the surface of the sample, and then a second light pulse (the probe beam) is directed to the same or an adjacent area at a later time. The retroreflector 229 shown in all of the illustrated embodiments 16–20 can be employed to provide a desired temporal separation of the pump and probe beams, as was described previously with regard to, by example, FIG. 9.

The system measures some or all of the following quantities: (1) the small modulated change $\Delta R$ in the intensity of the reflected probe beam, (2) the change $\Delta T$ in the intensity of the transmitted probe beam, (3) the change $\Delta P$ in the polarization of the reflected probe beam, (4) the change $\Delta\phi$ in the optical phase of the reflected probe beam, and/or (5) the change in the angle of reflections $\Delta\beta$ of the probe beam. These quantities (1)–(5) may all be considered as transient responses of the sample which are induced by the pump pulse. These measurements can be made together with one or several of the following: (a) measurements of any or all of the quantities (1)–(5) just listed as a function of the incident angle of the pump or probe light, (b) measurements of any of the quantities (1)–(5) as a function of more than one wavelength for the pump and/or probe light, (c) measurements of the optical reflectivity through measurements of the incident and reflected average intensity of the pump and/or probe beams; (d) measurements of the average phase change of the pump and/or probe beams upon reflection; and/or (e) measurements of the average polarization and optical phase of the incident and reflected pump and/or probe beams. The quantities (c), (d) and (e) may be considered to be average or static responses of the sample to the pump beam.

In a presently preferred embodiment the system provides for automatically focusing the pump and probe pulses to achieve predetermined focusing conditions, and the application of at least one calibration factor to the at least one transient response. This embodiment is especially useful when employed with time-evolved simulations and models of a structure of interest, which is a further aspect of this invention.

An important aspect of the operation of the picosecond measurement system concerns the precise relationship between computer simulations and the actual transient optical responses measured by the system. The following discussion describes the essential aspects of this relation for the particular example of a sample containing a number of planar films whose lateral extent is much greater than their thickness, and also greater than the linear dimensions of the region of the sample illuminated by the pump and probe pulses. A generalization of this discussion to laterally patterned structures will be evident to workers skilled in the relevant art, when guided by the following teachings. Similarly, the following discussion will consider, again as a specific example, a particular one of the transient optical responses, namely the change $\Delta R(t)$ in optical reflectivity. The generalization of the discussion to a consideration of the other transient optical responses aforementioned should also become evident to workers skilled in the relevant art, when guided by the following teachings.

In this example the computer simulations calculate the change in the optical reflectivity $\Delta R_{sim}(t)$ of the sample when it is illuminated with a pump pulse of unit energy per unit area of the sample. The simulation also gives a value for the static reflection coefficient of the pump and probe beams. The system measures the transient change $\Delta P_{probe-refl}$ in the power of the reflected probe pulse as determined, for example, by photodiode D1 in FIG. 18. It also measures the static reflection coefficients of the pump and probe beams from a ratio of the power in the incident and reflected beams. The incident probe power is measured by photodiode D2 in FIG. 18, the reflected probe power is measured by D1, the incident pump power is measured by D4, and the reflected pump power is measured by D3.

To relate the simulation results for the transient change in the optical reflectivity to the system measurement it is necessary to know: (a) the power of the pump and probe beams; (b) the intensity profiles of these beams; and (c) their overlap on the sample surface.

Let us suppose first that the pump beam is incident over an area $A_{pump}$ and that within this area the pump intensity is uniform. Then for each applied pump pulse the pump energy absorbed per unit area is $$\frac{P_{pump-inc}}{A_{pump}} \frac{(1-R_{pump})}{f} \quad (5)$$

where f is the repetition rate of the pump pulse train, and $R_{pump}$ is the reflection coefficient for the pump beam. Thus, the change in optical reflectivity of the each probe light pulse will be $$\Delta R_{sim}(t) \frac{P_{pump-inc}}{A_{pump}} \frac{(1-R_{pump})}{f} \quad (6)$$

and the change in power of the reflected probe beam will be $$\Delta P_{probe-refl} = P_{probe-inc} \Delta R_{sim}(t) \frac{P_{pump-inc}}{A_{pump}} \frac{(1-R_{pump})}{f} \quad (7)$$

In a practical system the illumination of the sample does not, in fact, produce a uniform intensity of the incident pump beam. Moreover, the intensity of the probe light will also vary with position on the sample surface. To account for these variations the equation for $\Delta P_{probe-refl}$ is modified to read $$\Delta P_{probe-refl} = P_{probe-inc} \Delta R_{sim}(t) \frac{P_{pump-inc}}{A_{effective}} \frac{(1-R_{pump})}{f} \quad (8)$$

where the effective area $A_{effective}$ is defined by the relation $$A_{effective} = \frac{\int I_{pump-inc}(\vec{r}) dA \int I_{probe-inc}(\vec{r}) dA}{\int I_{pump-inc}(\vec{r}) I_{probe-inc}(\vec{r}) dA} \quad (9)$$

where $I_{probe-inc}(\vec{r})$ and $I_{pump-inc}(\vec{r})$ are respectively the intensities of the probe and pump beams on the surface of the sample. One can consider $A_{effective}$ to be an effective area of overlap of the pump and probe beams.

Analogous expressions can be derived for the change in optical transmission $\Delta T(t)$, the change in optical phase $\Delta \phi(t)$, the change in polarization $\Delta P(t)$, and the change $\Delta \beta(t)$ in the angle of reflection of the probe light.

The following quantities are measured by the system: $\Delta P_{probe-refl}$, $P_{probe-inc}$, $P_{pump-inc}$, $R_{pump}$, $R_{probe}$. The computer simulation gives predicted values for $\Delta R_{sim}(t)$, $R_{pump}$, and $R_{probe}$. Thus the following comparisons can be made between the simulation and the system measurements in order to determine the characteristics of the sample.

(1) A comparison of the simulated and measured reflection coefficient $R_{pump}$.

(2) A comparison of the simulated and measured reflection coefficient $R_{probe}$.

(3) A comparison of the simulated and measured transient change $\Delta P_{probe-refl}$ in the power of the reflected probe light.

To make a comparison of the simulated and measured change, it can be seen from the preceding equation (8) that it is necessary to know the value of $A_{effective}$. This can be accomplished by one or more of the following methods.

(a) A first method directly measures the intensity variations of the pump and probe beams over the surface of the sample, i.e, $I_{probe-inc}(\vec{r})$ and $I_{pump-inc}(\vec{r})$ as a function of position, and uses the results of these measurements to calculate $A_{effective}$. This is possible to accomplish but requires very careful measurements which may be difficult to accomplish in industrial environment.

(b) A second method measures the transient response $\Delta P_{probe-refl}$ for a sample on a system S for which the area $A_{effective}$ is known. This method then measures the response $\Delta P_{probe-refl}$ of the same sample on the system S' for which $A_{effective}$ is to be determined. The ratio of the responses on the two systems gives the inverse of the ratio of the effective areas for the two systems. This can be an effective method because the system S can be chosen to be a specially constructed system in which the areas illuminated by the pump and probe beams are larger than would be desirable for an instrument with rapid measurement capability. Since the areas are large for this system it is simpler to measure the intensity variations of the pump and probe beams over the surface of the sample, i.e, $I_{probe-inc}(\vec{r})$ and $I_{pump-inc}(\vec{r})$ as a function of position. This method is effective even if the quantities which enter into the calculation of the simulated reflectivity change $\Delta R_{sim}(t)$ are not known.

(c) A third method measures the transient response $\Delta P_{probe-refl}$ for a sample in which all of the quantities are known which enter into the calculation of the simulated reflectivity change $\Delta R_{sim}(t)$ of the sample when it is illuminated with a pump pulse of unit energy per unit area of the sample. Then by comparison of the measured transient response $\Delta P_{probe-refl}$ with the response predicted from the Eq. 8 the effective area $A_{effective}$ is determined.

To build a truly effective instrument it is important that the effective area $A_{effective}$ be stable throughout the course of a sequence of measurements. To ensure this, the measurement system incorporates means for automatically focusing the pump and probe beams onto the surface of the sample so as to achieve a reproducible intensity variation of the two beams during every measurement. The automatic focusing system provides a mechanism for maintaining the system in a previously determined state in which the size and relative positions of the beams on the sample surface are appropriate for effective transient response measurements.

It should be noted that for any application in which the amplitude of an optical transient response is used to draw quantitative conclusions about a sample, a calibration scheme such as described above is an important feature of the measurement system.

The preceding description of the method for the comparison of the computer simulation results and the system measurements supposes that the several detectors in the measurement system are calibrated. It is contemplated that such a system will use detectors operating in the linear range so that the output voltage V of each detector is proportional to the incident optical power P. For each detector there is thus a constant G such that V=GP. The preceding description assumes that the constant G is known for each and every detector. In the case that this information is not available, the individual calibration factors associated with each of the individual detectors measuring $P_{probe-inc}$, $P_{pump-inc}$, and $\Delta P_{probe-refl}$ may be combined with $A_{effective}$ and f into a single overall system calibration constant C. Therefore in terms of a calibration factor C, Eq. 7 could be expressed as $$\Delta V_{probe-refl} = C\, V_{probe-inc} \Delta R_{sim}(t) V_{pump-inc} (1-R_{pump}) \quad (10)$$

where $\Delta V_{probe-refl}$ is the output voltage from detector used to measure the change in the power of the reflected probe light (D1), $V_{pump-inc}$ is the output voltage from the detector used to measure the incident pump light (D4), and $V_{probe-inc}$ is the output voltage of the detector used to measure the incident probe light (D2). Thus, to provide an effective instrument it is sufficient to determine the constant C. This can be accomplished by either of the following two methods.

(a) A first method measures the transient response $\Delta V_{probe-refl}$ for a sample in which all of the quantities are known which enter into the calculation of the simulated reflectivity change $\Delta R_{sim}(t)$ of the sample when it is illuminated with a pump pulse of unit energy per unit area of the sample. Next, the method measures $V_{probe-inc}$ and $V_{pump-inc}$, then determines $R_{pump}$ either by measurement or from the computer simulation. The method then finds the value of the constant C such that Eq. 10 is satisfied.

(b) A second method measures the transient response $\Delta V_{probe-refl}$ for a reference sample for which the transient optical response $\Delta R(t)$, when it is illuminated with a pump pulse of unit energy per unit area of the sample, has been measured using a system which has been previously calibrated, for example, by one or more of the methods described above. The method then measure $V_{probe-inc}$ and $V_{pump-inc}$, determines $R_{pump}$ by measurement, and then finds the value of the constant C such that the following equation is satisfied.

$$\Delta V_{probe-refl} = C\, V_{probe-inc} \Delta R(t) V_{pump-inc} (1-R_{pump}) \quad (11)$$

For both of these methods it is important to establish the autofocus conditions prior to making measurements of $\Delta V_{probe-refl}$, since C depends on the value of $A_{effective}$.

To summarize the heat generation and detection technique that is a feature of this invention, it has been shown above that it is possible to use the heat inducing and measuring system of this invention to determine the thermal impedance of an interface to the flow of heat (Kapitza resistance), and to then employ this measurement to characterize the interface in a systematic manner. The techniques of this invention can also be used to measure the heat flow in very small structures (e.g., nanostructures) and/or the thermal conductivity on which a small structure is deposited, and to then characterize the interface or interfaces of the structure, an issue of applied significance in, by example, techniques to optimize heat extraction from active electronic or optoelectronic devices.

Figure 8:
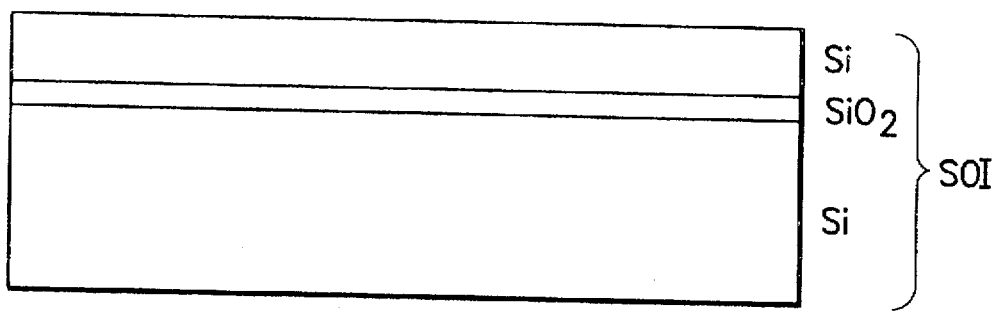
FIG. 8 is an enlarged, cross-sectional view of a silicon-on-insulator (SOI) sample that is amenable to characterization in accordance with this invention.

Further in accordance with the teachings of this invention, adhesion may be characterized by the determination of two different quantities in a single measurement or in a plurality of measurements. First, the acoustic reflection coefficient, at the very short acoustic wavelengths made possible by the teaching of this invention, is a sensitive indicator of bonding and atomic arrangements of an interface. Polymer layers as thin as a few A have been shown to have a profound influence on bonding between silicon and a metal. The second quantity is the thermal boundary (Kapitza) resistance which, as described above, can be obtained from the transient thermoreflectance. The Kapitza resistance is related to the acoustic reflection coefficients for all phonons incident from one material on another, and is thus useful in characterizing adhesion at the interface. By example, the characterization of the bonding of silicon to oxide can be used to evaluate preparation techniques such as BESOI (bond and etch back silicon-on-insulator). It is also within the scope of this invention to apply these techniques to silicon-on-insulator (SOI) and SIMOX structures of a type shown in FIG. 8, wherein an oxide layer (and hence interfaces) exists between two silicon layers.

Thus, while the invention has been particularly shown and described with respect to preferred embodiments thereof, it will be understood by those skilled in the art that changes in form and details may be made therein without departing from the scope and spirit of the invention.

What is claimed is:

1. A non-destructive system for characterizing an interface between two layers of a sample, comprising:

means for a generating a sequence of optical pump pulses at a frequency $f_1$ and for directing the sequence of pump pulses to an area of the surface of the sample;

means for generating a sequence of optical probe pulses at a frequency $f_2$ and for directing the sequence of probe pulses to a same or different area of the surface of the sample, wherein $f_1$ is not equal to $f_2$ for continuously varying a delay between the generation of a pump pulse and the generation of a probe pulse; and means for measuring, at a rate given by one of ($f_1$–$f_2$) or ($f_1$+$f_2$), at least one transient optical response of the structure to the sequence of pump pulses by detecting a change in a characteristic of a reflected or transmitted portion of the sequence of probe pulses, and for associating the detected change with a Kapitza resistance of the interface.

2. A non-destructive system for characterizing an interface between two layers of a sample, as in claim 1, wherein optical pump pulses are generated to have a first wavelength, and wherein optical probe pulses are generated to have a second wavelength that is a harmonic of the first wavelength.

3. A method for characterizing a sample, the sample having an interface between a substrate and at least one structure that is an intentionally or a non-intentionally formed layer or body that is disposed upon or within the substrate, comprising the steps of:

generating a reference data set of a transient optical response of the sample to an optical pump pulse, the reference data set being generated from at least one of (a) at least one reference sample or (b) a simulation of an interfacial response of a simulated sample;

applying a sequence of optical pump pulses and optical probe pulses to the sample;

comparing a measured transient optical response of the sample to the reference data set;

adjusting a value of the one or more characteristics of the sample so as to bring the reference data set into agreement with the measured transient optical response;

associating the adjusted value of the one or more characteristics with a value of one or more actual characteristics of the structure, at least one of said actual characteristics being a Kapitza resistance of the interface; and correlating the actual Kapitza resistance with microscopic and other properties of the interface, including at least one of the presence or absence of roughness, delaminations, defects, contaminants, adhesion, impurities, and undesirable interlayers.

4. A method as in claim 3, wherein the measured transient response includes at least one of a measurement of a modulated change $\Delta R$ in an intensity of a reflected portion of the probe pulse, a change $\Delta T$ in an intensity of a transmitted portion of the probe pulse, a change $\Delta P$ in a polarization of the reflected probe pulse, a change $\Delta \phi$ in an optical phase of the reflected probe pulse, and a change in an angle of reflection $\Delta \beta$ of the probe pulse.

5. A non-destructive system for characterizing an interface between two layers of a sample, comprising:

means for generating an optical pump pulse and for directing the pump pulse to an area of the surface of the sample;

means for generating an optical probe pulse and for directing the probe pulse to a same or different area of the surface of the sample so as to arrive after the pump pulse, wherein the pump pulse has the same wavelength as the probe pulse or a wavelength that is different than the wavelength of the probe pulse;

means for automatically controlling a focusing of the pump and probe pulses on the surface of the sample;

means for measuring at least one transient optical response of the structure to the pump pulse, the measured transient optical response comprising a measurement of at least one of a modulated change $\Delta R$ in an intensity of a reflected portion of the probe pulse, a change $\Delta T$ in an intensity of a transmitted portion of the probe pulse, a change $\Delta P$ in a polarization of the reflected probe pulse, aL change $\Delta \phi$ in an optical phase of the reflected probe pulse, and a change in an angle of reflection $\Delta \beta$ of the probe pulse;

means for calibrating the measurement system for a determination of an amplitude of the transient optical response of the sample; and means for associating an output of said means for measuring with a Kapitza resistance that is associated with said interface.

6. A non-destructive system for characterizing an interface as set forth in claim 5, and further a fiber optic for delivering at least one of the pump or probe pulses to the sample.

7. A non-destructive system for characterizing an interface as set forth in claim 5, and further comprising means for varying a location of said sample relative to at least one of said pump and probe pulses.

8. A non-destructive system for characterizing an interface as set forth in claim 5, wherein said pump and probe pulses are applied along parallel optical paths to a focussing objective that is disposed for focussing said pump and probe pulses on said sample, and are applied with one of a normal or oblique incidence angle to said sample.

9. A non-destructive system for characterizing an interface as set forth in claim 5, wherein one of said pump and probe pulses is applied to said surface of said sample with a normal incidence angle, and wherein the other one of said pump and probe pulses is applied to said surface of said sample with an oblique incidence angle.

10. A non-destructive system for characterizing an interface as set forth in claim 5, wherein said pump and probe pulses are derived from one of a single laser or separate lasers.

11. A non-destructive system for characterizing an interface as set forth in claim 5, wherein said pump and probe pulses are derived from a single laser pulse, and further comprising means for converting a wavelength of said single laser pulse to a harmonic of the wavelength such that one of the pump and probe pulses has a wavelength that differs from the wavelength of the other pulse.

12. A non-destructive system for characterizing an interface as set forth in claim 5, and further comprising means for impressing an intensity modulation on at least one of said pump and probe pulses, wherein said means for impressing is synchronized to a pulse repetition rate of a laser that generates said pump or probe pulses.

13. A non-destructive system for characterizing an interface as set forth in claim 5, and further comprising:

a continuous wave laser source for illuminating a portion of a surface of said sample with cw light; and means, responsive to reflected cw light, for performing an ellipsometric measurement of said sample.

14. A non-destructive system for characterizing an interface as set forth in claim 5, wherein said measuring means includes means for providing an image of the sample surface to an operator.

15. A non-destructive system for characterizing an interface as set forth in claim 5, wherein said pump and probe pulses are derived from first and second pulsed laser sources, respectively, and wherein a pulse repetition rate of said first laser source differs from a pulse repetition rate of said second laser source.

16. A non-destructive system for characterizing an interface as set forth in claim 5, and further comprising means for automatically varying a ratio of pump pulse energy to probe pulse energy.

17. A non-destructive system for characterizing an interface as set forth in claim 5, and further comprising means for focussing and translating said probe pulse on a surface of said sample independent of said pump pulse, wherein said focussing and translating means is comprised of a fiber optic having a tapered end diameter for performing near field focussing of said probe pulse, and means for translating said tapered end of said fiber optic relative to a focal spot of said pump pulse.

18. A non-destructive system for characterizing an interface as set forth in claim 5, wherein said sample is comprised of a plurality of patterned sub-structures having dimensions less than a focal spot diameter of either said pump or probe pulses, and wherein a plurality of said substructures are simultaneously illuminated by said pump and probe pulses.

19. A non-destructive system for characterizing an interface as set forth in claim 5, wherein said Kapitza resistance is associated with an adhesion property of at least one layer to another adjacent layer or to the substrate.

\* \* \* \* \*